United States Patent
Ermatov et al.

(10) Patent No.: US 10,792,624 B2
(45) Date of Patent: Oct. 6, 2020

(54) NITRIC OXIDE (NO) ACCUMULATION APPARATUS

(71) Applicant: BSN medical GmbH, Hamburg (DE)

(72) Inventors: Arthur Ermatov, Munich (DE); Karsten Hemmrich, Meerbusch (DE); Annahit Arshi, Hamburg (DE); Christian Schulze, Tostedt (DE)

(73) Assignee: BSN medical GmbH, Hamburg (DE)

( * ) Notice: Subject to any disclaimer, the term of this patent is extended or adjusted under 35 U.S.C. 154(b) by 463 days.

(21) Appl. No.: 15/566,354

(22) PCT Filed: Apr. 15, 2016

(86) PCT No.: PCT/EP2016/058454
§ 371 (c)(1),
(2) Date: Oct. 13, 2017

(87) PCT Pub. No.: WO2016/166347
PCT Pub. Date: Oct. 20, 2016

(65) Prior Publication Data
US 2018/0085717 A1   Mar. 29, 2018

(30) Foreign Application Priority Data
Apr. 16, 2015 (EP) .................................... 15163881

(51) Int. Cl.
*A61H 33/08* (2006.01)
*B01F 3/04* (2006.01)
(Continued)

(52) U.S. Cl.
CPC ..... *B01F 3/04248* (2013.01); *A61H 33/0087* (2013.01); *A61H 33/14* (2013.01);
(Continued)

(58) Field of Classification Search
CPC .............. B01F 3/04248; B01F 3/04262; B01F 3/04269; B01F 3/04985; B01F 15/00162; B01F 15/00175; B01F 15/0022
(Continued)

(56) References Cited

U.S. PATENT DOCUMENTS

| | | | |
|---|---|---|---|
| 7,377,499 B2 * | 5/2008 | Pakdaman | B01F 3/04262 261/122.1 |
| 2002/0082566 A1 * | 6/2002 | Stenzler | A61M 13/003 604/289 |
| 2006/0244160 A1 | 11/2006 | Pakdaman | |

FOREIGN PATENT DOCUMENTS

| | | |
|---|---|---|
| DE | 10227818 A1 | 1/2004 |
| EP | 0783896 A1 | 7/1997 |

(Continued)

OTHER PUBLICATIONS

Office Action dated May 6, 2020 for the corresponding Chinese Patent Application No. 201680035417.9.
(Continued)

*Primary Examiner* — Aaron F Roane
(74) *Attorney, Agent, or Firm* — Rankin, Hill & Clark LLP

(57) ABSTRACT

An NO-accumulation apparatus, method and use, comprising: a container (120) defining a cavity for accommodating a liquid (105), an inlet (150) for feeding the liquid into the container (120) and an outlet (151) for delivering the liquid from the container (120) to a bath unit; an NO-gas dissolving unit (140) for dissolving gaseous NO in the liquid (105) to produce an NO-containing liquid, wherein the NO-gas dissolving unit (140) is arranged in the container (120) and/or forms a part of the container (120); and an NO-gas port (110) in fluid communication with the NO-gas dissolving unit (140), wherein the NO-gas port (110) is adapted for coupling, particularly for releasably coupling, with an NO-gas (Continued)

supply, whereby the apparatus further comprises means for decoupling the inflow of NO to the liquid (105) within the container from the removal of the NO-containing liquid (NO-decoupling means), so that the removal of the NO-containing liquid is inhibited, when the NO is flowing into the liquid, and also the NO inflow is inhibited when the NO-containing liquid is removed from the container (105).

22 Claims, 15 Drawing Sheets

(51) Int. Cl.
*A61H 33/14* (2006.01)
*A61H 33/00* (2006.01)
*B01F 15/00* (2006.01)

(52) U.S. Cl.
CPC ...... *B01F 3/04262* (2013.01); *B01F 3/04269* (2013.01); *B01F 3/04985* (2013.01); *B01F 15/0022* (2013.01); *B01F 15/00162* (2013.01); *B01F 15/00175* (2013.01); *B01F 15/00422* (2013.01); *A61H 2033/145* (2013.01); *A61H 2033/146* (2013.01); *A61H 2201/0111* (2013.01); *A61H 2201/5058* (2013.01); *A61H 2201/5071* (2013.01); *A61H 2201/5082* (2013.01); *A61H 2201/5089* (2013.01); *B01F 2003/04312* (2013.01); *B01F 2003/04404* (2013.01); *B01F 2003/04921* (2013.01); *B01F 2215/0034* (2013.01); *B01F 2215/0431* (2013.01)

(58) Field of Classification Search
USPC .......................................................... 607/85
See application file for complete search history.

(56) References Cited

FOREIGN PATENT DOCUMENTS

| | | | |
|---|---|---|---|
| JP | H09253671 | A | 9/1997 |
| JP | 2005218571 | A | 8/2005 |
| JP | 2008264771 | A | 11/2008 |
| JP | 2011218265 | A | 11/2011 |
| JP | 2011245471 | A | 12/2011 |
| JP | 2012024726 | A | 2/2012 |
| JP | 2012076076 | A | 4/2012 |
| JP | 2013128876 | A | 7/2013 |

OTHER PUBLICATIONS

Notice of Reasons for Refusal dated Feb. 4, 2020 for corresponding Japanese Patent Application No. 2017-554335; English translation only.

* cited by examiner

Fig. 2A - C
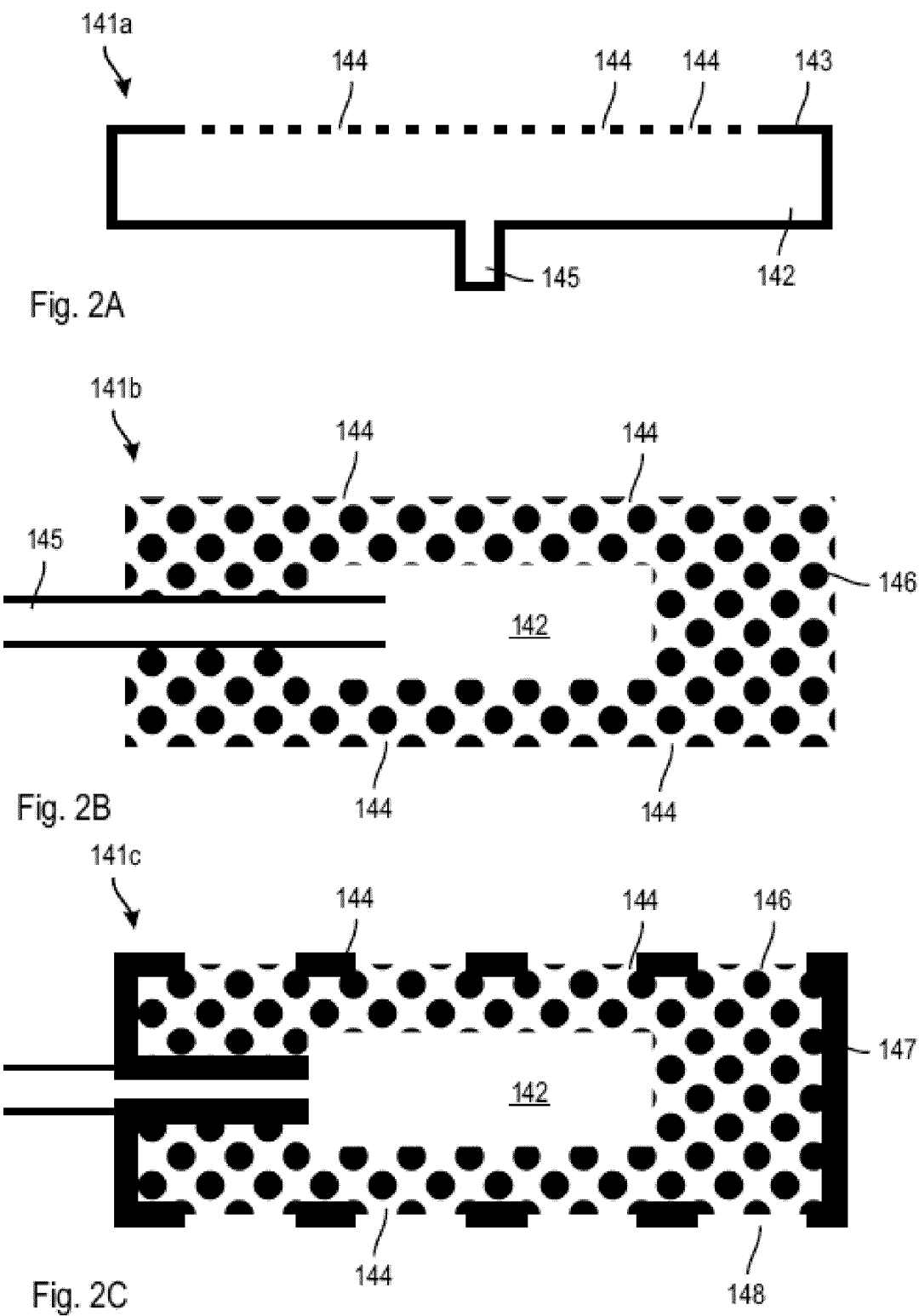

Fig. 2D – E

NITRIC OXIDE (NO) ACCUMULATION APPARATUS

TECHNICAL FIELD

Embodiments described herein relate to an NO-accumulation apparatus configured to accumulate gaseous NO in a liquid. Further embodiments relate to an NO-solution production apparatus which includes an NO-accumulation apparatus and a gaseous NO-supply or a gaseous NO-supply apparatus. Other embodiments relate to an NO-bath which includes an NO-solution production apparatus and an immersion apparatus for immersing body parts of a mammal or articles. Further embodiments relate to a method for accumulating NO in a liquid, and to the use of the NO-accumulation apparatus in the treatment of various diseases and for disinfecting articles.

BACKGROUND

The treatment of circulatory disorders and (chronic) wounds is a demanding challenge in everyday hospital life. Apart from conservative therapy with medicaments and wound dressings, other therapies can be used to relieve various aches and pains by stimulating the skin, provide relief from skin irritations, such as itching, and/or provide moisture to the skin.

In view of the foregoing, there is a need for further improvement.

SUMMARY

According to an embodiment, a NO-accumulation apparatus is provided which is configured to accumulate, i.e. dissolve, gaseous NO in a liquid.

According to an embodiment, an NO-accumulation apparatus for accumulating NO in a liquid includes a container defining a cavity for accommodating the liquid, an inlet for feeding the liquid into the container and an outlet for delivering the liquid from the container to a bath unit; an NO-gas dissolving unit for dissolving gaseous NO in the liquid to produce an NO-containing liquid, wherein the NO-gas dissolving unit is arranged in the container and/or forms a part of the container; and an NO-gas port in fluid communication with the NO-gas dissolving unit, wherein the NO-gas port is adapted for coupling, particularly for releasably coupling, with an NO-gas supply.

According to an embodiment the NO-accumulation apparatus further comprises means for decoupling the inflow of NO to the liquid 105 within the container 120 from the removal of the NO-containing liquid (so called "NO-decoupling means"), so that the removal of the NO-containing liquid is inhibited, when the NO is flowing into the liquid 105 of the container 120, and also the NO inflow is inhibited when the NO-containing liquid is removed from the container 120.

According to a preferred embodiment, said decoupling means of the NO-accumulation apparatus are mechanically, electrically or electronically coupled to allow the decoupling of the NO-inflow and the liquid removal and are preferably shut-off devices.

A mechanical coupling could be provided by gate valves which are coupled by an actuator so that the closing movement of the first gate valve is transduced to the second gate valve which is opened accordingly.

An electric or electronic coupling could be provided by an electrical connection, a radio communication or an electronic processing unit that regulates the NO-decoupling means in the above described manner.

In another embodiment the decoupling means could be provided by a pump which build up the required pressure of the NO gas in order to inflow into the container and/or by a pump that evacuate the NO-containing liquid from the container 105.

According to a further embodiment of the invention the shut-off devices are selected from the group consisting of valve, shutter valve, shutoff damper and stopcock.

According to an embodiment, an NO-solution production apparatus includes an NO-accumulation apparatus and a pressurized NO-gas supply coupled to the NO-gas port of the NO-accumulation apparatus.

According to an embodiment, an NO-bath apparatus includes an NO-accumulation apparatus or an NO-solution production apparatus, and a bath unit for accommodating an NO-containing liquid and for immersing one or more body parts of a mammal or a human, such as a patient, or articles into the NO-containing liquid.

According to an embodiment, an NO-bath apparatus is used for treating a medical condition.

According to an embodiment, a method for accumulating gaseous NO in a liquid includes providing a container; feeding a liquid into the container; feeding pressurized NO-gas into the liquid contained in the container, wherein a pressure within the container is optionally maintained at a pressure above ambient pressure, to accumulate NO in the liquid; and feeding the NO-accumulated liquid to a bath unit.

Further embodiments, aspects, advantages and features of the present invention are described in the dependent claims, the description and the accompanying drawings.

BRIEF DESCRIPTION OF THE DRAWINGS

The components in the figures are not necessarily to scale, instead emphasis being placed upon illustrating the principles of the invention. Moreover, in the figures, like reference signs designate corresponding parts. In the drawings:

FIGS. 2A to 2E illustrate various embodiments of NO-gas heads.

DETAILED DESCRIPTION

Reference will now be made in detail to the various embodiments, one or more examples of which are illustrated in the figures. Within the following description of the drawings, the same reference numbers refer to same or similar components. In the present disclosure, only the differences with respect to individual embodiments are described. Each example is provided by way of explanation and is not meant as a limitation. Further, features illustrated or described as part of one embodiment can be used on or in conjunction with other embodiments to yield yet a further embodiment. It is intended that the description includes such modifications and variations.

According to an embodiment, therapeutic agents such as nitric oxide (NO) can be added to a bath to provide a subject with a further therapeutic benefit. In mammals, NO is an important cellular signaling molecule involved in many physiological and pathological processes. NO is known to have several beneficial effects, including promoting vasodilation, having antimicrobial activity, reducing inflammation and participating in the wound healing process. In the latter, NO is known to play an important role by promoting angiogenesis through stimulation of vascular endothelial growth factor (VEGF) and increase fibroblast collagen synthesis.

Figure 1:
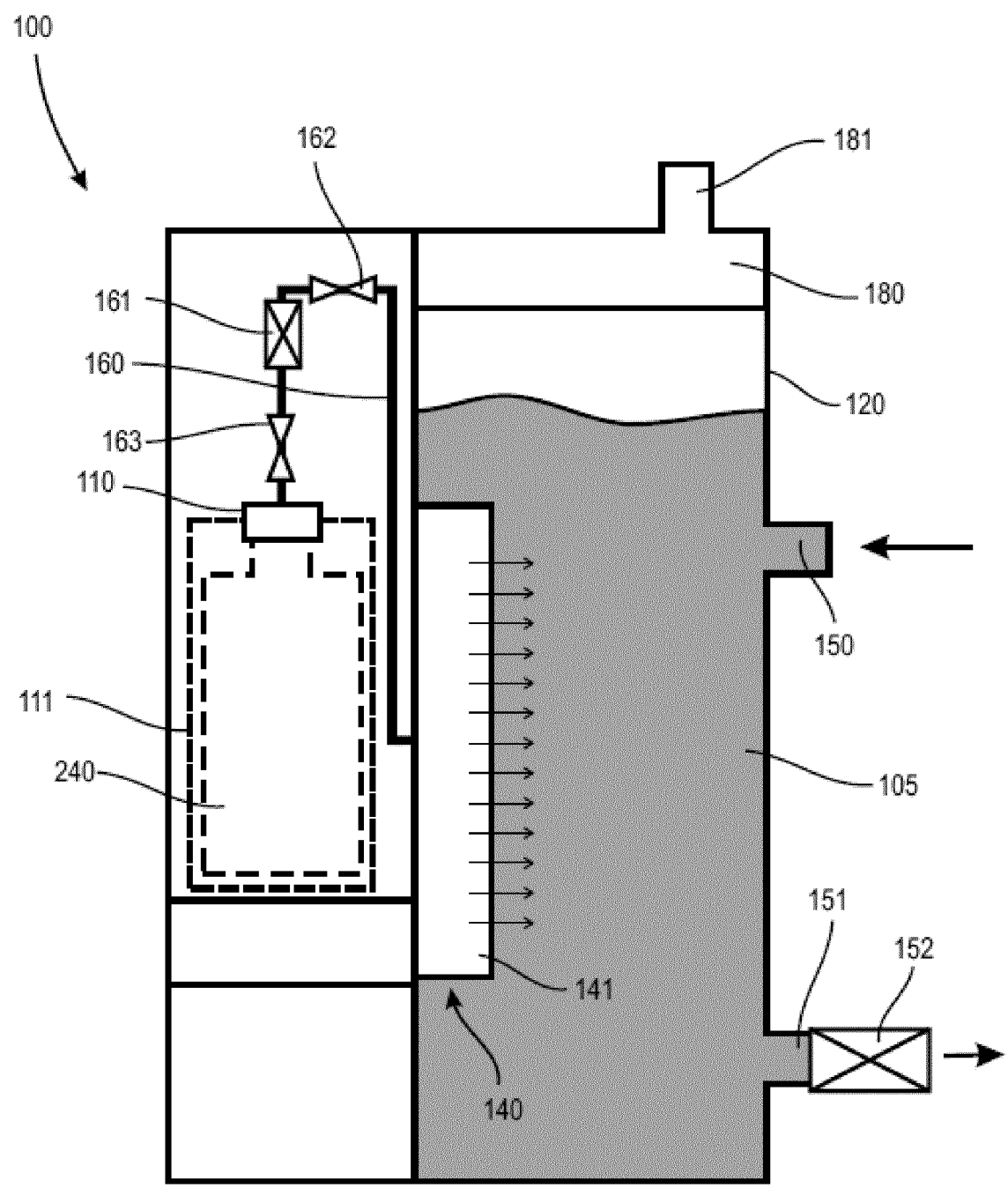
FIG. 1 illustrates a schematic perspective view of an NO-accumulation apparatus according to an embodiment described herein.

FIG. 1 illustrates an NO-accumulation apparatus 100 for accumulating NO in a liquid according to an embodiment. The NO-accumulation apparatus 100 includes a container 120 which defines a cavity for accommodating a liquid 105. More specifically, the container 120 can be formed by wall portions which define and encapsulate the cavity to form a closed tank. For example, the container 120 can have a circumferential side wall or circumferential side walls defining a cylindrical shape and top and bottom walls that close the cylindrically shaped container 120.

The container 120 can be adapted to be pressurized and to withstand a given working pressure above ambient pressure. For example, the wall portions of the container 120 and the shape of the container 120 can be adapted to withstand at least 100 kPa (1 bar) above ambient pressure, specifically at least 200 kPa, and more specifically of at least 300 kPa. A typical pressure range for operating the NO-accumulation apparatus 100 can be between 150 kPa and 500 kPa, particularly between 150 kPa and 300 kPa. The container 120 can also be adapted to withstand even higher pressures such as 800 kPa or even 1 MPa. Providing the container 120 with pressure-proof wall portions allows subjecting the liquid contained in the container 120 to a given pressure that facilitates dissolution of gaseous NO at a given temperature.

The liquid 105 can be, for example, an aqueous solution such as water. In the following embodiments, water is used as a liquid. However, the embodiments are not restricted to water. Other liquids which are capable of dissolving NO, such as buffered aqueous solutions, aqueous solutions containing salt and/or other components, and physiological solutions can be used as well.

The container 120 further includes an inlet 150 for feeding the water, i.e. the liquid, into the container 120 and an outlet 151 for delivering the water from the container 120 to a bath unit which will be described further below. According to an embodiment, the inlet 150 is adapted to be coupled with a liquid supply such as a water tank (liquid tank) or a pipe or hose such as a water pipe or water hose. The NO-accumulation apparatus 100 can thus function as a through-flow system with fresh water having substantially no NO dissolved therein fed to the inlet 150 and NO-accumulated or enriched water drawn from the outlet 151 to the bath unit or any other tank or vessel where the NO-containing water is stored or used.

In a further embodiment, the inlet 150 is in fluid communication with the bath unit, tank or vessel to provide a circulating-flow system with water contained in the bath unit, tank or vessel fed back into the container 120. The water 105 is thus circulating between the bath unit, tank or vessel and the container 120.

In the case that the water 105 is circulating between the bath unit, tank or vessel and the container 120, the NO-accumulation apparatus further comprises a circulation means 170 which can be any type of pump device suitably for pumping aqueous liquids such as e.g. any sort of positive displacement pump.

According to a preferred embodiment of the present invention, stable circulation of the NO-containing liquid is realized by using a positive-displacement metering pump having a self-priming ability as circulation pump device. This positive-displacement metering pump has a self-priming ability by which activation can be made in the initial operation without priming. Additionally, though NO-enriched water tends to generate bubble when its concentration increases, this positive-displacement metering pump can convey water stably even under bubble rich condition.

This positive-displacement metering pump is very effective particularly when correlation data between the circulation flow rate of the positive-displacement metering pump, the gas feeding pressure at aqueous liquid amount in container 120, the concentration of NO gas within the NO-enriched liquid in the container 120, and the circulation time are previously recorded, and, in producing the NO-enriched liquid, the circulation time is controlled based on the above-mentioned correlation data, to give a concentration of carbonic acid gas of carbonic water in a water tank in the range from 0.02 mmol/L and 0.2 mmol/L.

As the positive-displacement metering pump having a self-priming ability, a diaphragm pump, screw pump, tube pump or piston pump are preferred. Among recent commercially available products, a diaphragm pump is optimal from the standpoints of price, ability, size and the like. Specifically, there can be used, for example, a 3-head diaphragm pump manufactured by SHURflo (US), 5-head diaphragm pump manufactured by Aquatec Water System (US), 4-head diaphragm pump manufactured by FLOJET (US), and the like. These commercially available products are marketed usually as a booster pump in a beverage filtration apparatus.

According to an embodiment, the NO-accumulation apparatus further includes an NO-gas dissolving unit 140 for dissolving gaseous NO in the water, i.e. the liquid, to produce an NO-containing or NO-enriched water, i.e. NO-containing or NO-enriched liquid. The NO-gas dissolving unit 140 can be arranged in the container 120 and/or can form a part of the container 120, for example can form a wall portion of the container 120.

The NO-gas dissolving unit 140 provides an interface separating the water 105 from the gaseous NO. The interface is adapted to allow NO-gas to penetrate through the interface but substantially prevents the water from penetrating the interface.

According to an embodiment, the NO-gas dissolving unit 140 includes a an NO-gas head 141 with a plurality of openings through which NO-gas can flow or diffuse into the liquid 105. The flow of the NO-gas is illustrated in FIG. 1 by a plurality of arrows. The NO-gas head 141 can provide the interface through which the NO-gas is finely distributed over a large surface area to facilitate dissolution of the gaseous NO in the water 105.

According to an embodiment, the interface of the NO-gas dissolving unit 140 is a gas-flow interface which allows a gas flow through the interface different to approaches which use membranes that merely allow gas diffusion. A gas-flow interface is beneficial as the amount of gas which penetrates the interface can be directly controlled by adjusting the pressure difference over the interface. Different thereto, the amount of gas which penetrates a diffusion-controlled interface, for example a gas diffusion membrane, mainly depends on the concentration difference over the interface and only to a lesser extent on the pressure difference. As the pressure difference can be directly and more easily controlled in comparison to the concentration difference, a gas-flow interface improves the NO-gas accumulation in the water and facilitates the control of the final NO-concentration in the water 105.

A diffusion through a membrane can be described by the first Fick's law of diffusion where the diffusion flux is proportional to the concentration gradient and the surface area through which diffusion takes place. Different thereto, the volume flux of a gas flow through an opening is proportional to the area of the opening (or the total area of the openings) and the pressure difference. The saturation concentration of the NO-gas is also pressure-dependent and increases with the partial pressure of NO-gas. It is therefore desirable to use a gas-flow interface and to operate the NO-gas dissolving unit 140 at high pressure to improve the NO-dissolution in the water 105.

In one embodiment of the invention, the NO-permeable membrane representing the gas-flow interface is a stacked layer of two or more membranes segregating the NO-gas compartment from the liquid compartment. By use of a membrane staple a large membrane surface area is provided allowing a more efficient gas supply. Accordingly, this might be used to decrease the NO overpressure.

In an alternative embodiment the NO-permeable membrane is formed as a hollow fiber membrane. For an efficient supply of NO a set of hollow fibers is used, providing an enlarged membrane surface in a small space. Suitably, hollow fiber membranes are packed into cartridges which can be incorporated within the apparatus of the invention, preferably within the liquid container. The membrane hollow fibers could be used in an inside-out mechanism, whereby the NO gas is led through the hollow fibers and the liquid is given in the compartment outside the hollow fibers. Alternatively, the membrane hollow fibers are used in an outside-in mechanism, whereby the liquid flows through the hollow fibers and the gas is provided in the compartment surrounding the fibers.

The hollow fiber membranes are suitably made from artificial polymers which include e.g. cellulose acetate, polysulfone, polyethersulfone, and polyvinylidene fluoride.

When a hollow fiber membrane is used in NO-accumulation apparatus, any material may be used, as this hollow fiber membrane, providing it is excellent in gas permeability, and a porous membrane or nonporous gas permeability membrane (hereinafter, abbreviated as "non-porous membrane") may be used. As the porous hollow fiber membrane, those having an opening pore diameter on its surface of 0.01 to 10 μm are preferable. A hollow fiber membrane containing a non-porous membrane is also suitably used. The most preferable hollow fiber membrane is a complex hollow fiber membrane of a three-layer structure comprising a non-porous layer in the form of thin membrane both sides of which are sandwiched by porous layers. As its specific example, for example, a three layer complex hollow fiber membrane (MHF, trade name) manufactured by Mitsubishi Rayon Co. Ltd. is mentioned.

In a preferred embodiment, a non-porous layer is formed as a very thin membrane excellent in gas permeability, and porous layers are formed on its both surfaces, to protect the non-porous layer so that it is not injured. Here, the non-porous layer (membrane) is a membrane through which a gas permeates by a mechanism of dissolution and diffusion into a membrane substrate, and any membrane can be used providing it contains substantially no pore through which a gas can permeate in the form of gas like Knudsen flow of molecules. When this non-porous membrane is used, a gas can be supplied and dissolved without discharging a NO gas in the form of bubble into the aqueous liquid, therefore, efficient dissolution is possible, additionally, a gas can be dissolved simply under excellent control at any concentration. Further, there is no counterflow which occurs uncommonly in the case of a porous membrane, namely, warm or hot aqueous liquid does not counter-flow to the gas feeding side through fine pores.

The thickness of a hollow fiber membrane is preferably 10 to 150 μm. When the membrane thickness is 10 μm or more, sufficient membrane strength tends to be shown. With a membrane thickness of 150 μm or less, sufficient NO gas permeation speed and dissolving efficiency are possible. In the case of a three-layer complex hollow fiber membrane, the thickness of a non-porous membrane is preferably 0.3 to 2 μm. When the membrane thickness is 0.3 μm or more, the membrane does not easily deteriorate, and leak due to membrane deterioration does not occur easily. With a membrane thickness of 2 μm or less, sufficient carbonic acid gas permeation speed and dissolving efficiency is given.

When the water passing amount per hollow fiber membrane module is 0.2 to 30 L/min and the gas pressure is 0.01 MPa to 0.3 MPa, it is preferable that the membrane area is about 0.1 $m^2$ to 15 $m^2$.

As the membrane material of a hollow fiber membrane, for example, silicone-based, polyolefin-based, polyester-based, polyamide-based, polysulfone-based, cellulose-based and polyurethane-based materials and the like are preferable. As the material of a non-porous membrane of a three-layer complex hollow fiber membrane, polyurethane, polyethylene, polypropylene, poly(4-methyl-1-pentene), polydimethylsiloxane, polyethylcellulose and polyphenylene oxide are preferable. Among them, polyurethane manifests excellent membrane forming property and provides little eluted substance, therefore, it is particularly preferable.

The internal diameter of a hollow fiber membrane is preferably 50 to 1000 μm. With an internal diameter of 50 μm or more, the flow route resistance of fluid flowing in a hollow fiber membrane decreases appropriately, and feeding of fluid becomes easy. With an internal diameter of 1000 μm or less, the size of a dissolving apparatus can be decreased, providing a merit in compactness of the apparatus.

In a further embodiment of the invention, the NO-accumulation apparatus comprises a stirring device which is preferably located in the container 120. This stirring device supports the rapid preparation of a homogenous NO-enriched aqueous liquid. The stirring device can be any type of device suitably for stirring aqueous liquids such as e.g. a magnetic stirrer, a paddle mixer, a spiral mixer or a planetary mixer.

Moreover, a gas-flow interface allows applying an initial gas burst to deliver a large gas volume to the water 105. This enhances the initial NO-gas dissolution and shortens the time needed to dissolve a given amount of NO-gas to reach a desired final NO-concentration.

A further improvement can be seen when the NO-gas is dissolved under pressure in the water 105, for example at a pressure of at least 50 kPa above ambient pressure, particularly at a pressure of at least 100 kPa above ambient pressure, and more particularly at a pressure of at least 200 kPa above ambient pressure. In further embodiments, the dissolution of NO occurs at a pressure of at least 300 kPa above ambient pressure, or even at a pressure of at least 500 kPa above ambient pressure or of at least 1 MPa above ambient pressure.

To provide, for example, an initial burst, the pressure at which NO-gas is supplied into the container 120 and/or the flow rate can be temporally increased. This can shorten the time needed to reach a desired NO-concentration in the water.

Furthermore, dissolving NO-gas at high pressure also reduces NO-gas losses. Since the NO-gas is introduced under high pressure and the water in the container 120 is kept at higher pressure, more NO-gas dissolves in comparison to an NO-gas dissolution at ambient pressure. Hence, less NO-gas simply "bubbles" through the water and can escape.

For illustration purposes, to reach an NO-gas concentration of about 1 mmol in the water 105 at ambient pressure (about 100 kPa), a significant higher NO-gas flow would be needed in comparison to the case at a pressure of about 1 MPa (about 10 bar). At 100 kPa, most of the NO-gas would remain gaseous and would "bubble" through the water 105 without dissolving while at about 1 MPa, most if not all of the NO-gas would dissolve. Dissolving NO-gas at higher pressure thus reduces the amount of NO-gas needed to produce a desired NO-concentration. This is also beneficial in view of safety requirements as the risk that NO-gas escapes can be reduced.

According to an embodiment, a temporal NO-gas profile is provided by varying the NO-gas pressure. Dissolved NO decomposes at a given rate. Therefore, NO is typically delivered continuously, for example at a constant rate after an initial gas burst. In an embodiment, the NO-gas pressure is increased from an initial constant rate to a higher rate to increase the concentration of NO dissolved in the water 105, i.e. the liquid, over time.

According to an embodiment, the NO-accumulation apparatus 100 further includes an NO-gas port 110 in fluid communication with the NO-gas dissolving unit 140. The NO-gas port 110 is adapted for coupling, particularly for releasably coupling, with an NO-gas supply 240.

The NO-gas port 110, which is simply referred to as the gas port, can include a quick-release coupling for coupling and uncoupling of the NO-gas supply 240.

The quick-release coupling can include, according to an embodiment, a thread coupling for screwing the NO-gas supply 240 into or onto the gas port 110. The gas port 110 can include, for example, in inner thread and the NO-gas supply 240 can include an outer thread for engaging with the inner thread of the gas port 110.

According to a further embodiment, the NO-gas supply 240 can be accommodated in a carrier unit 111 which forms a part of the quick-release coupling of the gas port 110. The carrier unit 111 can, for example, engage with a thread of the gas port 110 and thus keeps the NO-gas supply 240 reliably in place and in operational engagement with the gas port 110. For example, the carrier unit 111 can press the NO-gas supply 240 against a sealing member of the gas port 110 when the carrier unit 111 fully engages with the thread of the gas port 110.

FIG. 1 illustrates a carrier unit 111 in engagement with the gas port 110 for holding and pressing the NO-gas supply 240 against the gas port 110.

The carrier unit 111 and the NO-gas supply 240 are illustrated by dashed lines as both are optional elements of the NO-gas accumulation apparatus 100. The NO-gas supply 240 together with the NO-gas accumulation apparatus forms an NO-solution production apparatus as is described in more detail further below. The carrier unit 111 can form a part of the quick-release coupling of the gas port 110 and can be part of the NO-gas accumulation apparatus 100.

Typically, engagement elements of the carrier unit 111 engage with corresponding engagement elements of the gas port 110 to hold and fix the carrier unit 111 with the NO-gas supply 240 in place and to ensure that a gas-tight coupling is provided between the NO-gas supply 240 and the gas port 110. The engagement elements of the carrier unit 111 and of the gas port 110 are part of the quick release coupling.

According to a further embodiment, the quick-release coupling can include a clamping lever coupling which is adapted to couple the carrier unit 111 with the gas port 110 or with engagement means of the gas port 110. The lever, for example, can be articulated at the gas port 110 and pushes the carrier unit 111 and therefore the NO-gas supply 240, when pressed down, towards the gas port 110 for providing a gas-tight coupling by pressing a gas outlet port of the NO-gas supply 240 against a sealing member arranged at the gas port 110.

According to a further embodiment, the quick-release coupling can include a bayonet coupling which is adapted to couple the carrier unit 111 with the gas port 110. The bayonet coupling can additionally include a lock mechanism that prevents the bayonet coupling unintentionally releasing. A lock mechanism for preventing unintentional release can also be provided for the other quick-release couplings described above.

According to an embodiment, the NO-gas supply 240 is a gas bottle with a defined volume. For example, the volume of the gas bottle and the amount of NO-gas contained therein can be adapted to be sufficient for one medical treatment. For illustration purposes only, a medical treatment, for example for bathing a limb such as a foot in about 10 l of NO-containing water for about 30 min, only few liter of NO-gas is needed. As the NO-gas is compressed on the gas bottle, the actual volume of the gas bottle can be 0.5 l or less.

An example of the NO-gas supply 240 is a gas cartridge having a safety sealing cap that is activated when a piercing element such as a hollow needle advances through the sealing cap. The gas cartridge can be accommodated in the carrier unit 111 which is coupled with corresponding engagement means of the gas port 110 to push the gas cartridge with its sealing cap ahead against the piercing element that opens or ruptures the sealing cap. The pressurized NO-gas contained in the gas cartridge leaves the gas cartridges after rupture of the sealing cap and is fed to the container 120 to be dissolved in the water 105 contained in the container 120.

The safety sealing cap can be a one-time used (single use) sealing cap that needs to be replaced when refilling the cartridge. In further embodiments, the sealing cap includes a one-way value, also referred to as a check valve, that prevents NO-gas from escaping the gas cartridge when the one-way valve is not activated. Activation can include a displacement of a piston or ball of the one-way valve when the gas cartridge is pressed against the gas port 110 which includes an engagement element that acts against the piston or wall and pushes the piston or wall relative to the advancing movement of the gas cartridge into the opposite direction. Examples of one-way valves include ball check valves or piston check valves which can be spring-loaded.

As further illustrated in FIG. 1, the NO-accumulation apparatus further includes, according to an embodiment, an NO-gas feeding 160 that includes the gas port 110. The NO-gas feeding 160, hereinafter simply referred to as gas feeding 160, provides a fluid communication between the gas port 110 and the NO-gas dissolving unit 140. When the NO-gas supply 240 is coupled with the gas port 110, the gas feeding 160 establishes a controllable fluidic communication between the NO-gas supply 240 and the NO-gas dissolving unit 140, particularly with the NO-gas head 141.

To provide a controllable fluidic communication, the gas feeding 160 can include at least one pressure reducer 161 and a controllable valve 162 arranged downstream of the pressure reducer 161. The pressure reducer 161 reduces the pressure of the NO-gas from the pressure at which the NO-gas is released from the NO-gas supply 240 to a working pressure at which the NO-gas is fed into the water 105. The control valve 162 can be used, in an embodiment, merely to open and close the fluidic communication and thus to allow or prevent the NO-gas from being delivered to the NO-gas head 141.

In a further embodiment, the control value 162 also functions as a flow control valve to adjust the amount of gas that flows to the NO-gas head 141. The control 162 can therefore be used to temporarily increase or decrease the NO-gas flow, for example to provide an initial NO-gas burst for quickly raising the NO-concentration in the water 105.

The gas feeding 160 can further include a high-pressure value 163 on the upstream side of the pressure reducer 161 for controlling the gas flow to the pressure reducer. The high-pressure valve 163 can be adapted to function as a safety valve to close the gas feeding 160 if an overpressure or any other unwanted operation condition is detected. Typically, the high-pressure value 163 remains closed until a sealed coupling between the gas port 110 and the NO-gas supply 240 has been established. The control valve 162 can be referred to as low-pressure valve 162.

If needed, the pressure reducer 161 can include two stages or can be provided by two pressure reducers 161 provided sequentially in the gas feeding 160 if the pressure reduction is very large.

The working pressure of the NO-gas, i.e. the pressure at which the NO-gas is fed to the NO-gas dissolving unit 140 can depend on the pressure maintained in the container 120. For example, the pressure within the container 120 can be slightly above ambient pressure so that the NO is dissolved in the water 105 at ambient pressure. To improve and speed up the NO-dissolution, the internal pressure in the container 120 can be set to a value higher than the ambient pressure such as 100 kPa, 200 kPa, 300 kPa, 500 kPa or more above ambient pressure. The NO-gas is then delivered at a pressure higher than the internal pressure in the container 120, for example at a pressure of 50 kPa or more above the pressure within the container 120.

A higher NO-gas pressure on the downstream side of the pressure reducer 161 in comparison to the internal pressure within the container 120 is also desired to ensure that the NO-gas can penetrate the interface provided by the NO-gas head 141. The NO-gas head 141 having a plurality of small openings functions as a flow resistor and thus a given pressure is desired to press the NO-gas through the interface of the NO-gas head 141.

The pressure reducer 161 can be controllable for adjusting the downstream side pressure, which is also referred to as the low-pressure side or low-pressure branch of the gas feeding 160. Typically, the downstream side pressure is maintained at a given pressure and the control valve 162 is controlled to adjust the gas flow. If, for example, a higher or lower pressure in the downstream side is desired, the pressure reducer 161 is operated to adjust the pressure. Both the pressure reducer 161 and the control valve can be controlled by a central controller 220, which is described further below.

According to an embodiment, the NO-accumulation apparatus 100 can be adapted to maintain a pressure above ambient pressure in the container 120 and to dissolve the NO-gas in the water, i.e. the liquid 105, under pressure above ambient pressure. The outlet 151 is preferably connected to, or comprises, a pressure reducer 152 to reduce the pressure of the liquid or water 105 contained in the container 120 to ambient pressure.

As the NO-accumulated water 105 is intended to be applied to a bath unit, the pressurized water 105 is first depressurized. This can be done by the pressure reducer 152 in a controlled manner so that the pressure of the water 105 after the pressure reducer 152 is either at or only slightly above ambient pressure.

In the event that NO partially degasses during depressurization of the NO-containing water 105, a gas collecting unit 153 can be coupled downstream to the pressure reducer 152 which collects the outgassed NO. The gas collecting unit 153 can also function as water collecting tank for temporarily storing the NO-enriched water 105. Since NO is comparatively unstable, the NO-containing water 105 is typically not stored for a very long time such as hours. The temporal storing will by typically in the range of few minutes. This time would also be sufficient for excess NO to outgas.

Collecting outgassed NO is beneficial in terms of safety as NO is a harmful and poisonous gas despite its medical relevance. Outgassing into ambient air should therefore be avoided and appropriate measures taken to prevent this. Connecting the gas collecting unit 153 downstream of the NO-accumulation apparatus 100 is therefore advisable, particularly if NO was dissolved in the water under high pressure to speed up dissolution.

The gas collecting unit 153 can also optionally form part of the NO-accumulation apparatus 100 and thus be integrated into a common housing so that only the outlet port 154 downstream of the gas collecting unit 153 is accessible for the personnel who use the NO-accumulation apparatus to provide a NO-containing bath for medical or other purposes.

The outgassed NO can be fed from the gas-collecting unit 153 into an NO-removal unit 180 via a NO-gas return feeding 157 for removing excess NO that is not dissolved in the water 105. The NO-removal unit 180 is described further below.

To reduce the amount of NO-gas that can outgas after the NO-enriched or accumulated water 105 is depressurized to ambient pressure, the desired final NO-concentration is set to be lower than the saturation concentration of NO in the liquid. For example, NO has a solubility of about 60 mg/l (about 2 mmol/l) at 20° C. at ambient pressure. The final NO-concentration is set significantly lower than this saturation concentration which further reduces the risk of outgassing NO. For example, the final NO-concentration can be set to about 1 mmol/l, or to about 0.5 mmol/l or even less. For many therapeutic treatments, an NO-concentration between 0.02 mmol/l and 0.2 mmol/l is sufficient.

With reference to FIGS. 2A to 2C, embodiments of the NO-gas head 141 are described.

In a first embodiment as illustrated in FIG. 2A, an NO-gas head 141a comprises a chamber 142 having a wall 143 for separating the NO-gas from the liquid or water 105. The wall 143 includes a plurality of nozzles 144 which forms the plurality of openings of the NO-gas head 141a. The NO-gas head 141a also include an inlet port 145 which is coupled with the gas feeding 160 for feeding the NO-gas into the chamber 142.

The size of the nozzles 144, i.e. the cross-sectional area of each of the nozzles, is comparably small to prevent water inflow into the chamber 142. Furthermore, small-sized nozzles 144 also prevent the formation of large gas bubbles. To increase the total gas flow through the interface formed by the wall 143 containing the nozzles 144, the number of nozzles 144 and the size of the wall 143 can be designed appropriately. For example, the size, i.e. diameter, of each nozzle can be in a range of about 5 μm to about 200 μm, particularly between about 10 μm to about 100 μm, and more particularly between 20 μm and 60 μm. More generally, the lower limit of the nozzle size (diameter) can be about 2 μm, 4 μm, 6 μm, 8 μm, 10 μm, 12 μm, 15 μm, or 20 μm. The upper limit of the nozzle size (diameter) can be about 500 μm, 400 μm, 300 μm, 200 μm, 150 μm, 100 μm, 90 μm, 80 μm, 70 μm, 60 μm, 50 μm, 40 μm, 30 μm, or 20 μm. Basically, any combination of the above mentioned lower limits with any of the above mentioned upper limits is possible such as 4 μm to 70 μm, 8 μm to 40 μm, 12 μm to 30 μm, 6 μm to 30 μm, to name a few.

The total cross-sectional area provided by the nozzles 144 can be in a range between 1 $mm^2$ to 100 $mm^2$, between 1 $mm^2$ to 20 $mm^2$, between 1 $mm^2$ to 5 $mm^2$, or between 0.5 $mm^2$ to 5 $mm^2$. When a large number of nozzles 144 are provided, they are typically distributed over a large area to increase the available interface area provide by the NO-gas head 141a. The size of the interface area, i.e. the area over which the nozzles 144 are distributed, can be from about 100 $mm^2$ to about 10000 $mm^2$ or even larger. It is desirable to increase the interface area while keeping the nozzle size, i.e. the effective opening area of each nozzle 144, small.

The volume flow of gas through a nozzle mainly depends on the pressure difference over the nozzle, i.e. the pressure difference between the NO-gas in the NO-gas head and the pressure within the container, and the opening area of the nozzle. The geometrical shape and length of the nozzle also influence the volume flow. It is therefore possible to adapt the total volume flow of NO-gas through the NO-gas head by adjusting the size of the nozzles and/or the number of the nozzles which are provided by the NO-gas head.

To increase the wall area provided with the nozzles 144, the chamber 142 can be formed by tubes or interconnected pipes with the walls of the tubes and pipes be provided with the nozzles. The larger the number of nozzles 144, the smaller the nozzles 144 can be which is beneficial in terms of NO-dissolution and prevention of gas bubble formation.

A further embodiment of an NO-gas head 141b is illustrated in FIG. 2B. The NO-gas head 141b includes a porous body 146 that forms a porous portion of the NO-gas head 141b. The porous body 146 is provided with open-cell porosity with interconnected pores to allow a gas flow, or gas diffusion, from an internal chamber 142 of the porous body 146 to the exterior of the NO-gas head 141b. The internal chamber 142 can be formed to distribute the NO-gas to different portions of the porous body 146 so that the gas flow is evenly distributed through the porous body 146. The internal chamber 142 does not need to have a large volume as the main function of the internal chamber 142 is to distribute the NO-gas within the porous body. To increase the stability of the porous body 146, a plurality of interconnected internal chambers 142 can be formed with thick wall portions between adjacent chambers 142 which mechanically stabilize the porous body 146.

An inlet port 145 coupled with the gas feeding 160 extends up to the internal chamber 142. A sealing can be provided between the outer wall of the inlet port 145 and the porous body 146 to prevent leakage of NO-gas.

The interconnected pores 144 of the porous body 146 provide the openings of the NO-gas head 141b and improve distribution of the NO-gas over a large area. The size and shape of the porous body 146 can be determined according to specific needs. For example, the porous body 146 can have a cylindrical shape with a cylindrical internal chamber 142 extending substantially co-axially to the porous body 146. To increase the available area for diffusing the NO-gas, a plurality of porous bodies 146 can be provided in which each is in fluid communication with the gas feeding 160.

According to an embodiment, the porous body 146 can have a porosity, i.e. the ratio of the total volume of the pores to the total volume of the material of the porous body 146 (i.e. volume of the internal chamber excluded) from about 5% to about 90%, particularly from about 15% to about 70%, and more particularly from about 20% to 50%. In a further embodiment, the porosity can be from about 40% to 90%, and particularly from 50% to 80%.

According to an embodiment, the mean pore size, i.e. diameter, of the pores 144 can be in the same range as given above for the nozzles.

Both the porosity and the mean pore size can influence the gas flow through the porous body 146. A further parameter is the thickness of wall portions of the porous body 146 through which the NO-gas flows from the internal chamber 142 to the exterior. The total hydraulic resistance of the porous body 146 can be adapted by appropriately selecting the porosity, the pore size and the wall thickness of the porous body.

To reduce the hydraulic resistance against the gas flow, the wall thickness can be made small. If the mechanical stability of the porous body 146 might be affected, an external support 147 can be provided as illustrated in FIG. 2C showing a NO-gas head 141c according to a further embodiment. The external support 147 includes openings 148 which are significantly larger than the pores 144.

Figure 2D:
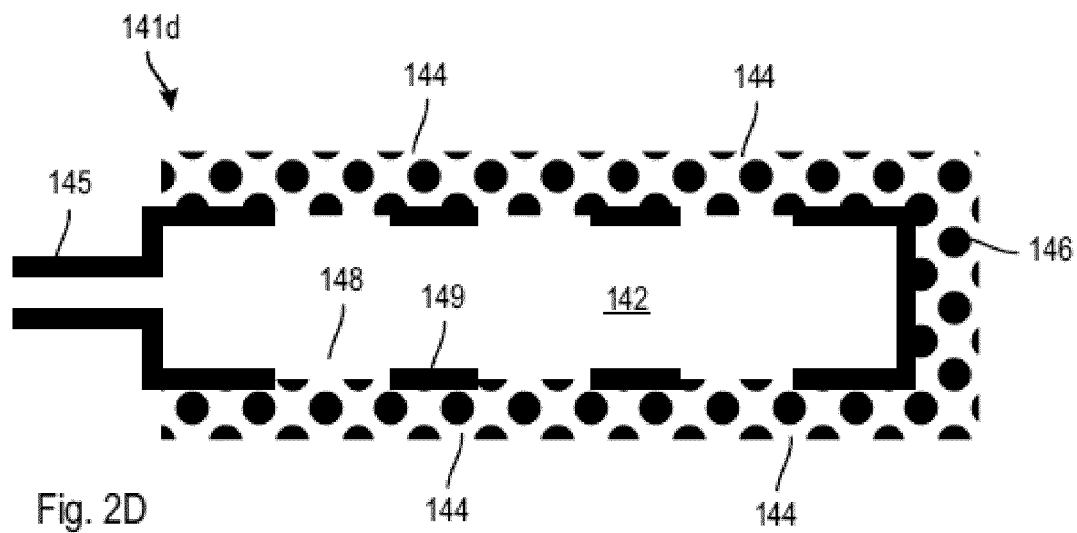

In a further embodiment, as illustrated in FIG. 2D, an internal support 149 is provided which carries the porous body 146 at its external surface. The internal support 149 can be, for example, a pipe or any other hollow part which includes a plurality of openings 148 which are larger than the pores 144 of the porous body 146. The internal support 149 can also define the internal chamber 142 of the NO-gas head 141d. An example of an internal support 149 is a tube having openings through which the NO-gas can flow into the porous body 146. To provide a large surface for NO-dissolution, a plurality of tubes each having a porous body 146, or porous portion, formed at the external surface of the tubes can be used.

According to a further embodiment, the NO-gas head 141 can include an internal and an external support which sandwich a porous body. It is also possible to provide a porous portion or body on the wall 143 of the NO-gas head 141a in FIG. 2A. In this case, the large openings are formed in the wall and the pores of the porous body or portion form the openings of the NO-gas head 141.

The openings or pores 144 of the NO-gas head 141 also form a gas flow limiting element which has a given hydraulic resistance against the gas flow. This additional hydraulic resistance may be taken into consideration when adjusting the pressure on the low-pressure side of the gas feeding 160.

Figure 2E:
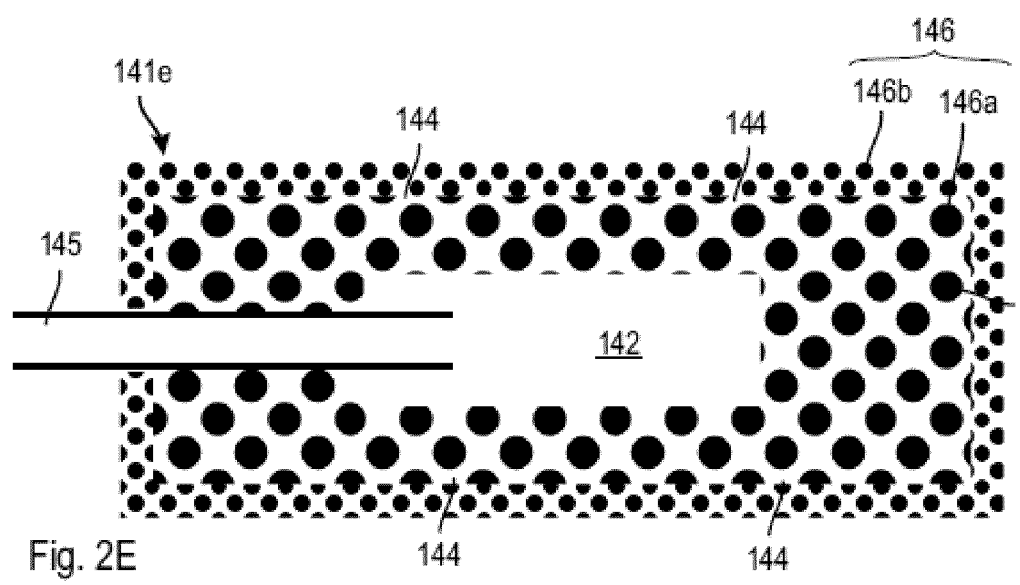
Figure 3:
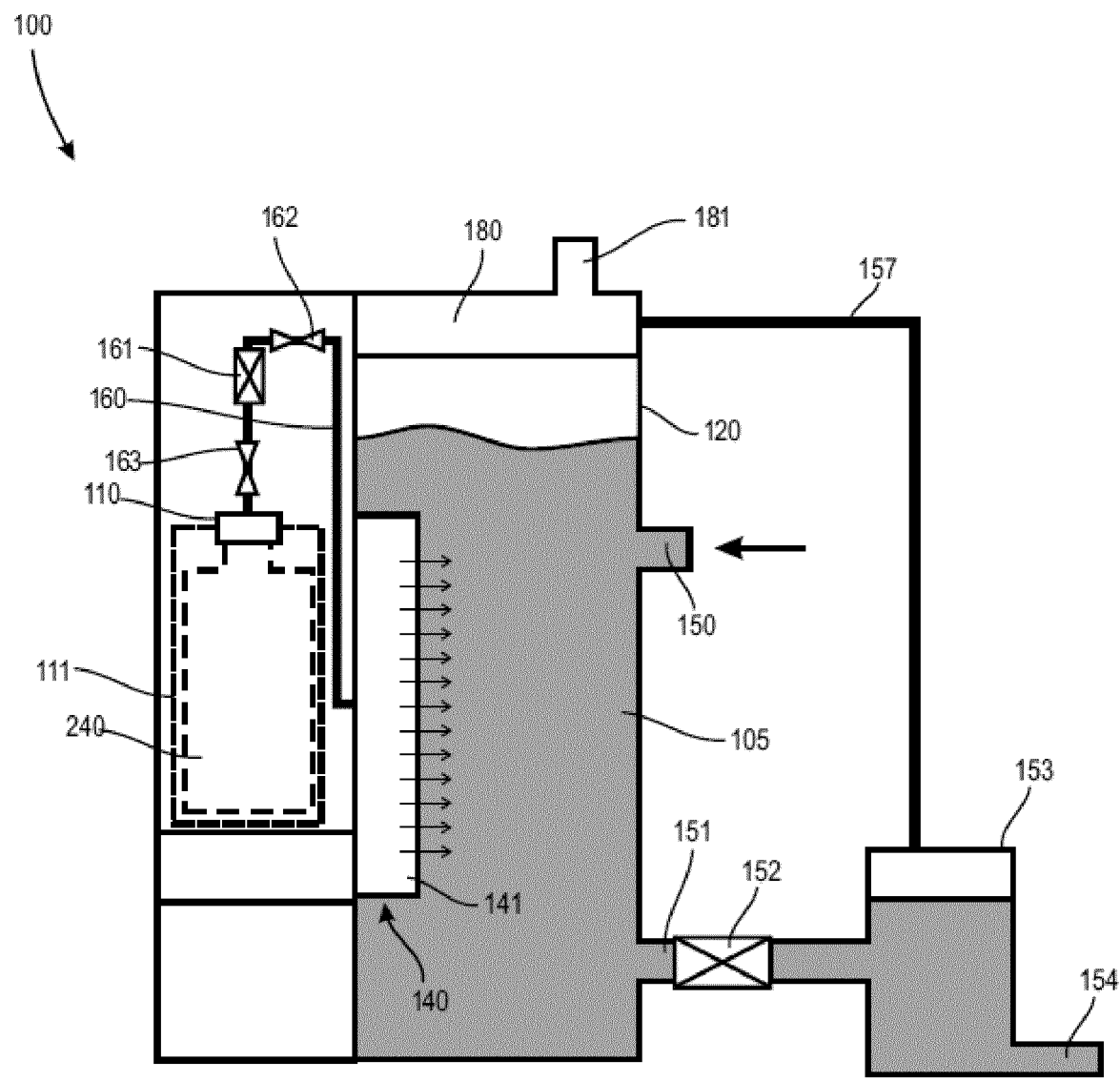
FIG. 3 illustrates a schematic perspective view of an NO-accumulation apparatus according to an embodiment described herein.

According to a further embodiment, as illustrated in FIG. 2E, the porous body or portion 146 includes an inner porous layer or body 146a and an outer porous body or layer 146b. The outer porous layer 146b and the inner porous layer differ in at least one of the medium pore size, the porosity, and the material. For example, as illustrated in the embodiment of FIG. 2E, the outer porous layer 146b has smaller pores than the inner porous layer 146a. Both porous layers 146a, 146b can have the same porosity and can be formed of the same material.

According to an embodiment, the material of the porous body 146 or of each of the inner and outer layers 146a, 146 can be selected from various ceramic materials. Examples are alumina, fused silica, silicon carbide, zirconia, cordierite, forsterite, magnesia stabilized zirconia, yttria-stabilized zirconia, and mullite. The material for the porous body 146 or the porous layers 146a, 146b can also be referred to as ceramic foam.

According to an embodiment, the material of the porous body 146 or of each of the inner and outer layer 146a, 146 can be selected from various metallic materials, which are also referred to as metal foam. Examples are stainless steel, nickel-containing alloys such as Ni—Cu alloys, Hastelloy™, Inconel™, and Monel™, or titanium foam. Ni-based alloys are very corrosion resistant also in an acidic environment.

The above-mentioned porous materials are inorganic materials having a high mechanical stability and typically also a high inertness with respect to chemical attacks. According to an embodiment, the metal and ceramic materials can be combined to form a composite. The composite can have a sandwich structure with a metallic porous material and a ceramic porous material.

Porous materials can be provided in virtually any outer form due to the means of production. Porous unburned materials such as slickers can be spray-coated onto a carrier such as the internal support 149. Furthermore, porous bodies can be formed by isostatic pressure manufacturing and also by additive manufacturing such as so-called 3D-printing.

The porosity of the porous material can be adjusted by selecting the particle size, the amount of pore forming material that burns off during sintering, and the sintering time.

Porous inorganic materials can also be formed by fiber material such as glass fibers or by other inorganic fiber materials.

According to a further embodiment, the porous material is an organic material. Porous organic materials can be formed, for example, by a fiber materials comprised of PE (polyethylene) and/or PET (polyethylene terephthalate) fibers. Other possible materials are high-molecular polyethylene (UHMWPE), high-density polyethylene (HDPE), polypropylene (PP), polytetrafluoroethylene (PTFE), polyvinylidene fluoride (PVDF), ethylene-vinylacetate (EVA), polyethersulfone (PES), polyurethane (PU), polycarbonates (PC), polyamides (PA), thermoplastic polyurethanes (TPU) and copolymers and/or compound materials of the above mentioned polymers.

According to an embodiment, the porous material is formed of an organic or inorganic fiber material.

According to a further embodiment, the frit is formed by sintered glass powder. The nominal pore width of the glass frit, i.e. the medium pore width, can be for example between 1 μm and 500 μm, particularly between 1 μm and 160 μm, more particularly between 1 μm and 100 μm, and even more particularly between 1 μm and 40 μm. The pore size can also be in the ranges given above for the nozzle 144.

According to an embodiment, the NO-gas dissolving unit 140 includes a membrane that provides, or forms at least a part of, the interface for the controlled flow of NO-gas. The membrane can be a non-porous membrane that provides for a diffusion-control permeation of NO-gas. Furthermore, the membrane can be a NO-selective membrane which only allows penetration of NO. NO-selective membrane can be formed of Nafion, which is a sulfonated tetrafluoroethylene based fluoropolymer-copolymer, polycarbazole, polystyrene, fluorinated xerogels, or PTFE.

The NO-accumulation apparatus as described herein is beneficial particularly for use in therapeutic applications, such as in clinical treatment of wounds ambulant care.

The NO-accumulation apparatus as described herein avoids, or at least allows to significantly reduce, that NO is an erroneously supplied which could lead to an undesired overdose or underdose of NO on the target body portion. Moreover, the NO-accumulation apparatus as described herein further avoids or reduces that NO is environmentally exposure and thus minimizes health damage, e.g. acute headaches in patients and hospital staff, and in extreme cases, death.

Health damages could include contamination of the eyes which could lead to severe injury and swelling of the eye tissue. As exposure to NO-gas in low concentrations produces an irritating effect on the mucous membranes of the eyes, nose, throat and lungs, which can include choking, coughing, headache, nausea and fatigue, the NO-accumulation apparatus reliably prevents the water being saturated with NO which would lead to an NO-evaporation. Particularly the NO-removal unit 180 ensures that excess and not dissolved NO is removed.

Other health problems, which are avoided when using the NO-accumulation apparatus, include over-exposure to NO that may cause methemoglobinemia, cyanosis, delayed pulmonary edema, mental confusion, unconsciousness and death. High concentrations of NO-gas may cause an oxygendeficient atmosphere; however, other more significant health effects will occur prior to those for oxygen deficiency. NO can react in the body to oxidize hemoglobin to methemoglobin in the blood. Coma and death can ensue when methemoglobin levels reach 70%. The inability of methemoglobin to combine with oxygen can result in clinical effects due to tissue hypoxia. Symptoms include muscular tremors, drowsiness, a brownish-blue hue to the mucous membranes, increased heart rate, vertigo and vomiting.

Other problems associated with the usage of uncontrolled NO-baths that are avoided or reduced by the NO-accumulation apparatus described herein relate to more practical aspects. For instance, the storage of large NO-gas container is rather difficult in hospital due to shortage of space. Treating bedridden patients is also a problem due to the limited mobility of those baths. Connecting a large NO-gas bottle to a bath via tubes is error-prone and may be complex for hospital staff. Further, such baths require thorough cleaning after each and every patient session which is both time-consuming and difficult to handle for the hospital staff.

The NO-gas supply 240 has therefore, according to an embodiment, a volume that is adapted to include only the amount of NO-gas needed for one bath treatment. Such a treatment may last for about 20 to 40 minutes, typically about 30 minutes. Since the water 105 is disposed for hygienic reasons as it may become biologically contaminated during bathing of limbs or other body parts, the water 105 is not reused. The NO-gas supply 240 can therefore be comparably small and light and provided in cartridges which can be easily replaced by hand. This also ensures that the amount of NO-gas is comparably small which adds to the safety of the NO-accumulation apparatus in comparison to approaches which use large bottles that need to be reliably fixed to a wall to prevent the bottle falling.

Using small, easily replaceable NO-gas supplies 240 also allows providing the NO-accumulation apparatus as mobile medical apparatus that can be carried by medical personnel or even by a patient.

According to an embodiment, the NO-removal unit 180 includes an NO-adsorber that physically adsorbs NO which is not dissolved. The NO-removal unit 180 is in fluid communication with the volume of the container 120 so that excess NO, which is not dissolved in the liquid or water 105 and which escapes from the water or liquid 105 contained in the container 120, flows through the NO-removal unit 180 and is thereby inactivated, removed or decomposed.

The NO-adsorber 180 can include a porous metal surface or a porous metal body acting as adsorber. In a particular aspect, the porous metal surface or porous metal body has a specific area of at least 100 m²/g. A large surface to volume ratio is beneficial for improving the adsorption capacity.

The NO-removal unit 180 can also form an upper part of the container 120, for example to close the container 120 at its upper end. The NO-removal unit 180 can be provided as a removable lid for opening and closing the container 120 which facilitates cleansing of the container 120 and removal and repair of the NO-dissolution unit 140 if needed.

In a further embodiment, the NO-removal unit 180 can be separate to the container 120 but in fluid communication therewith through a pipe or tube which can be a fixed or flexible pipe, hose or tube. To provide a mobile and easy to handle apparatus, the container 120, NO-removal unit 180 and NO-gas supply 240 can be accommodated in a common housing. Alternatively, the NO-removal unit 180 and NO-gas supply 240 can be adapted to be fixed to the exterior of the container 120.

According to an embodiment, the porous metal surface of the NO-removal unit 180 can include alumina. A porous alumina surface can include pellets which are formed of a combination of activated alumina and binders. For example, the porous alumina pellets can have a nominal pellet diameter of from 1 to 5 mm, particularly from 2 to 4 mm. The porous alumina pellets can also have a bulk density of from 0.1 to 2 g/cm³, preferably from 0.5 to 1 g/cm³. Further, the porous alumina pellets can be impregnated with an oxidizing agent, such as sodium or potassium permanganate ($NaMnO_4$/$KMnO_4$).

According to a further embodiment, the porous metal surface includes a manganite alloy. Typically, the manganite alloy is a nonstoichiometric nickel-copper manganite.

In a further embodiment, the porous metal surface includes nickel (Ni) (100), such as a Ni (100) crystal, Fe, such as $Fe_2O_3$ or $Fe_3O_4$, or Si such as Si (111). Further alternative NO-adsorbers which can be used include silica supports combined with triethanolamine or active carbon.

The NO-adsorber can be operated, according to an embodiment, at temperatures between −20° C. to 150° C., particularly between 0° C. to 100° C., more particularly between 10° C. and 50° C.

According to an embodiment, the NO-adsorber is combined with a ventilator which forces the NO-gas to gather at or to flow through the NO-adsorber. Typically, the ventilator can operate at an air speed performance of 0.30 to 2.54 m/s. The above described combination of NO-adsorber and ventilator provides highly effective removal capacities of NO.

When the NO-accumulation apparatus 100 is operated at a pressure above ambient pressure, no additional ventilator is needed as the pressure difference could be beneficially used to form a gas flow from the container 120 through the NO-removal unit 180 to a gas outlet 181 of the NO-removal unit 180. The gas outlet 181 can be provided with, or coupled with, a pressure reducer that prevents the excess NO-gas flowing at high rate through the NO-removal unit 180 and the pressure dropping within the container 120. It is also possible to provide a pressure reducer in the fluid communication between the interior of the container 120 and the NO-removal unit 120.

The NO-removal unit 180 can include, according to an embodiment, a catalytic system that reduces NO. Catalytic systems for reducing NO may operate at elevated temperatures and thus the NO-removal unit 180 can be provided with a heater.

According to an embodiment, the water, i.e. the liquid 105, can contain at least one of the following ingredients: catalyst, detergent, buffer, substance having chromophoric groups, solution stabilizer, substance which increases the half-life of NO, antioxidant, colorant, pH-indicator, skin care agent, flavor, gas formation agent and pharmacologically active agent.

According to an embodiment, the water, i.e. the liquid 105, can contain at least one pharmacologically active agent selected from the group consisting of anti-inflammatory agents such as NSAIDS, corticoids, immunosuppressive agents, antibiotics, anticoagulants, antithrombotic, antiviral agents, antifungal agents, local anesthetics and analgesics.

According to an embodiment, the liquid 105 can contain at least one antioxidant selected from the group consisting of tocopherole, tocotrienole, tocomonoenole, butylated hydroxyanisole (BHA), butylated hydroxytoluene (BHT), glutathione, cysteine, thiolactic acid, ascorbic acid, alpha-lipoic acid, hydroxycinnamic acids such as p-coumaric acid, ferulic acid, sinapinic acid, caffeic acid, hydroxybenzoic acids such as gallic acid, anthocyanins, flavonoids, phytoestrogens, ascorbates, thiols and free radical scavengers.

According to an embodiment, the liquid 105 can contain a gas formation agent such as a carbonate salt which releases $CO_2$ via acidification.

According to an embodiment, the liquid 105 can contain an antioxidant.

According to an embodiment, the liquid 105 can contain at least one solution stabilizer such as dimethyl sulfoxide or ethanol.

According to an embodiment, the liquid 105 can contain at least one skin care agent such as dexpanthenol or an extract form aloe vera.

According to an embodiment, the liquid 105 is an isotonic buffered aqueous solution.

According to an embodiment, the liquid 105 has a pH value from 3.0 to 10, preferably from 5.5 to 7.4, more preferably from 6.0 to 7.0.

According to a further embodiment, the liquid 105 can contain water, at least one buffer for adjusting the pH value of the liquid 105 to a range from 6.0 to 7.4 and 50 to 250 mM of an antioxidant.

According to a particular embodiment, the liquid 105 can contain water, 8 g/L NaCl, 0.2 g/L KCl, 1.424 g/L $Na_2HPO_4$ and 0.2 g/L $KH_2PO_4$.

According to another particular embodiment, the liquid 105 can contain water, 8 g/L NaCl, 0.2 g/L KCl and 50-250 mM of a mixture of acetic acid and sodium acetate.

According to a further embodiment, the ingredients of the liquid 105 are provided in a pre-portioned form such as powder, granule, tablet, dragee, soft gelatin capsule, hard gelatin capsule, suspension, emulsion, paste, cream, ointment, gel or lotion. This pre-portioned form provides good patient compliance.

According to a particular embodiment, the ingredients of the liquid 105 are provided in the form of an effervescent tablet. In this form they are resolved quickly and enrich the medium also with the $CO_2$.

According to an embodiment, the pre-portioned form of the ingredients comprises vials, bottles, sachets or tubes.

Some of the above mentioned ingredients can be added to the liquid already in the container 120 or the liquid 105 which is fed into the container 120 can already contain one, few or all of the final ingredients. For example, the water 105 can already contain a buffer and/or an antioxidant when fed to the container 120 or these ingredients can be added to the water contained in the container 120. These ingredients facilitate NO-dissolution in the water 105 and reduce NO-decomposition which is beneficial for reducing the NO-gas volume needed for a particular bath treatment.

As described above, according to an embodiment, the NO-accumulation apparatus 100 includes a gas port 110 configured to be coupled with a gaseous NO-supply apparatus 240 or NO-gas supply 240. Additionally or alternatively, the NO-accumulation apparatus 100 can include a container 120 which includes gas dissolving unit 140 for dissolving gaseous NO supplied from a gaseous NO-supply apparatus 240 in the liquid 105 contained in the container 120. Additionally or alternatively, the NO-accumulation apparatus 100 can include at least one NO-removal unit 180 for removing excess NO such as a catalytic system for the reduction of NO. Additionally or alternatively, the NO-accumulation apparatus includes at least one NO-sensor configured to determine the NO-concentration. Additionally or alternatively, the NO-accumulation apparatus includes a container having at least one inlet and at least one outlet. The at least one inlet is configured to add liquid into the container. The at least one outlet is configured to remove liquid from the container into an immersion apparatus for immersing body parts of a mammal or articles.

According to a further embodiment of the present disclosure, a NO-solution production apparatus is provided. The NO-solution production apparatus includes a NO-accumulation apparatus as described herein to form a NO-solution, a gaseous NO-supply apparatus configured to supply gaseous NO, and gas dissolving unit configured to feed the gaseous NO from the gaseous NO-supply apparatus into the NO-accumulation apparatus.

According to a further embodiment of the present disclosure, a NO-bath is provided. The NO-bath includes a NO-solution production apparatus as described herein, and an immersion apparatus for immersing body parts of a mammal or articles.

According to a further embodiment of the present disclosure, a method is provided for accumulating NO in a liquid. The method includes the steps of feeding gaseous NO from a gaseous NO-supply into a NO-accumulation apparatus with the help of gas dissolving unit, and accumulating gaseous NO in the liquid.

According to a further embodiment of the present disclosure, the NO-accumulation apparatus configured to accumulate gaseous NO in a liquid can be used in the treatment of diseases.

According to an embodiment, the NO-accumulation apparatus is configured to accumulate gaseous NO in a liquid, wherein the NO-accumulation apparatus includes a gas port configured to be coupled with a gaseous NO-supply apparatus.

As used herein, the expression "NO-accumulation apparatus" may refer to an apparatus in which gaseous NO can be accumulated in a liquid. Typically, gaseous NO can be accumulated up to a maximal concentration, which can be, for example, 60 mg/l at 20° C. in an aqueous liquid. Typical liquids are aqueous liquids such as water, pH-buffered aqueous liquids, and slat-containing water.

Figure 4:
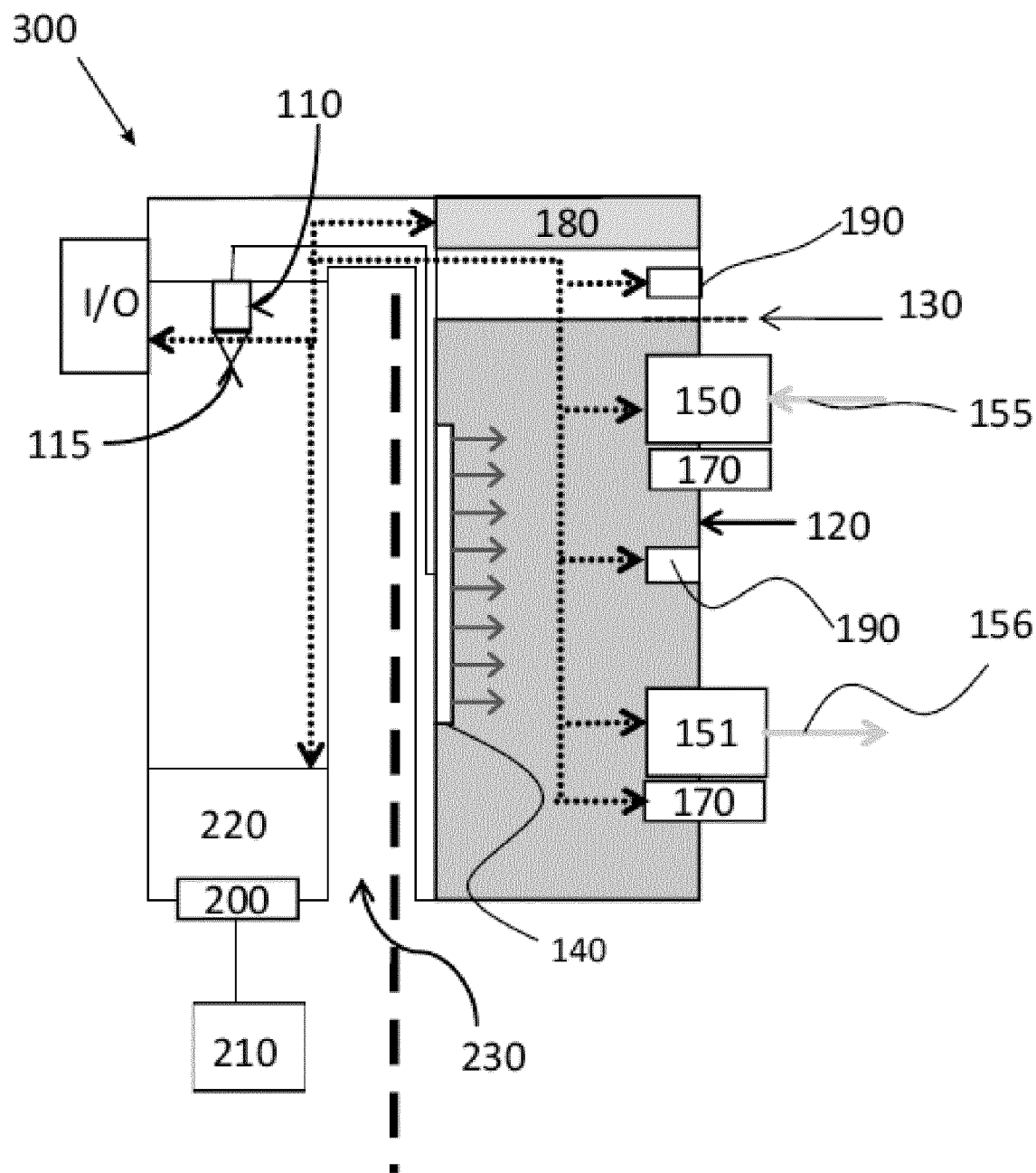
FIG. 4 illustrates a schematic perspective view of an NO-solution production apparatus according to an embodiment described herein.

With reference to FIG. 4, an NO-accumulation apparatus 300 according to a further embodiment which is configured to accumulate gaseous NO in a liquid is exemplarily shown. It is noted that same reference signs refer to the same or similar parts or features. The NO-accumulation apparatus 300 also includes a NO-gas supply to form an NO-solution production apparatus.

As illustrated, the NO-accumulation apparatus 300 includes a gas port 110. The gas port 110 is configured to couple with a gaseous NO-supply apparatus (not shown). For instance, as illustrated, the gas port 110 may include a thread 115 (see FIG. 4) on which the gaseous NO-supply apparatus can be mounted. Alternatively, the gas port 110 may include a hose connection to which one end of a hose can be detachably connected while the other end of the hose can be detachably connected to the gaseous NO-supply apparatus.

The NO-accumulation apparatus 300 as exemplarily illustrated in FIG. 4 may further include a container 120. The container 120 may extend along an axial direction and may include or consist of one or more portions which are a non-detachably connected with each other. The container 120 may further include at least one cap which is detachably connected to the one or more portions. For instance, in a particular aspect, the container 120 may include five portions, such as a bottom portion and four side portions in the shape of an open box. In this particular aspect, the container may further include a cap which is detachably connected to the five portions and which is configured to provide a sealed container. By detaching the cap from the one or more portions, liquid can be added to the container before NO is accumulated in the container. In an alternative aspect, the container 120 may consist of six portions which are non-detachably connected with each other, such as a bottom portion, a top portion and four side portions in the shape of a sealed box (closed box). Typically, the container 120 includes a volume of from 5 to 100 l, 10 to 100 l, preferably from 30 to 80 l, more preferably from 40 to 60 l. The container 120 may also include a labelling 130 which indicates the maximum amount of liquid to be added to the container 120.

Typically, the container 120 of the other embodiments can have a similar volume. A typical volume is in the range from about 10 l to about 20 l.

The container 120 may further include gas dissolving unit 140. The gas dissolving unit 140 is configured to feed gaseous NO from the gaseous NO-supply apparatus into the container. In a particular aspect, the gas dissolving unit 140 are nozzles through which gaseous NO can be fed into the container. In a particular aspect, the nozzles are arranged in a predetermined pattern such that they are equally spaced from one another and possess a generally uniform size and shape. In an alternative aspect, the gas dissolving unit is a porous material, such as a foam, through which gaseous NO can be fed into the container.

The container 120 may further include at least one inlet 150 and at least one outlet 151. Typically, the at least one inlet 150 is configured to add liquid (water inflow 155) into the container 120 whereas the at least one outlet 151 is configured to remove liquid (water outflow 156) from the container 120 into an immersion apparatus (not shown) for immersing body parts of a mammal or articles. For instance, one end of a hose can be detachably connected to the at least one inlet 150 while the other end of the hose can be detachably connected to a liquid supply, such as a water supply. The at least one outlet 151 may be an opening through which the liquid can flow out of the container 120.

Additionally or alternatively to the at least one inlet 150 and outlet 151, the container 120 may include water circulation means 170. These water circulation means 170 can circulate water in the NO-accumulation apparatus 300. Typically, the water circulation means 170 are water circulation turbines.

The NO-accumulation apparatus 300 as exemplarily illustrated in FIG. 4 may further include at least one catalytic system 180 for the reduction of NO. Typically, the catalytic system 180 is a selective catalytic reduction system (SCR). This SCR can catalyze the reduction of non-dissolved gaseous NO present in the container to $N_2$, $H_2O$ and $CO_2$. In a particular aspect, the catalytic system 180 is positioned on the inner side of the top portion of the container or on the inner side of the cap.

The NO-accumulation apparatus 300 as exemplarily illustrated in FIG. 4 may further include a NO-absorber 180 configured to absorb gaseous NO. Typically, the NO-absorber 180 includes a material which can absorb gaseous NO. In a particular aspect, the NO-absorber is positioned on the inner side of the top portion of the container or on the inner side of the cap.

The NO-accumulation apparatus 300 as exemplarily illustrated in FIG. 4 may further include at least one NO-sensor 190 configured to determine the NO-concentration. In a preferred aspect, the NO-accumulation apparatus includes an NO-sensor 190 which determines the concentration of gaseous NO in a gas, such as air. Additionally or alternatively, the NO-accumulation apparatus includes an NO-sensor 190 which determines the concentration of gaseous NO dissolved in a liquid, such as water.

The NO-sensor 190 for detecting NO dissolved in the liquid 105 can be an electrochemical NO sensor. The electrochemical NO-sensor can be based on electrooxidation of NO on metal surfaces or electroreduction of NO on metal surface.

The electrochemical NO-sensor can include an electrolyte-filled microtube which includes both a platinum working and a silver reference electrode. The microtube or pipette is sealed with a thin gas-permeable membrane that allows diffusion of NO. Upon application of a potential to the electrodes a current can be determined which is proportional to the NO-concentration.

Another type of electrochemical NO-sensor 190 can include a solid permselective NO-electrode that can be formed by modifying a noble metal or carbon electrode with a permeable membrane. The selectivity of the sensor can be improved by providing a plurality of membranes.

Another type of electrochemical NO-sensor 190 can include solid catalytic electrodes. The catalytic electrodes can contain a mediator (e.g., metalloporphyrins and metal phthalocyanines) which is capable of catalyzing the oxidation or reduction of NO. This reduces interference from other electroactive species.

NO-selective membranes useful for the NO-sensor 190 can be formed of Nafion, which is a sulfonated tetrafluoroethylene based fluoropolymer-copolymer, polycarbazole, polystyrene, fluorinated xerogels, or PTFE.

The NO-accumulation apparatus 300 as exemplarily illustrated in FIG. 4 may further include a connector 200 configured to couple with a power supply 210. Typically, the power supply 210 may be an on grid or off grid power supply. A typical on grid power supply may be a battery.

The NO-accumulation apparatus 300 as exemplarily illustrated in FIG. 4 may further be controlled by a controller 220. The controller 220 can be part of a controller unit that can additionally include a user interface to allow the personnel to operate the NO-accumulation apparatus 300 and a display unit for displaying various operational parameters such as the NO-gas pressure, the pressure within the container 120, the temperature of the water 105 within the container 120, and the remaining time if a timer for a treatment has been set. The personnel can, for example, set a desired final NO-concentration and the controller 220 can set based on the set parameter of the final NO-concentration and experimental or empirical values a pressure and/or NO-gas flow profile to enrich the water with NO so that the desired NO-gas concentration is obtained in a short time.

The control unit can be connected to any sensor that is provided and to any operational means such as heater 250 or water circulation means 170. Any of the following sensors can be provided: the NO-sensor 190, a pH sensor 270, at least one pressure sensor (for the NO-gas pressure and/or for the pressure within the container 120 and/or for the pressure within the NO-gas removal unit 180) and a temperature sensor 280.

The NO-accumulation apparatus 300 as exemplarily illustrated in FIG. 4 may further include a coupling member 230 configured to couple with an immersion apparatus or bath unit (not shown). The coupling member 230 can form an U-shape which provides a space for mounting the NO-accumulation apparatus 300 onto the immersion apparatus or to mount the NO-accumulation apparatus 300 partially into a bath unit. For example, the coupling member 230 can connect the container 120, or the housing which contains the container, with the gas supply and keeps the gas supply 240 and the container 120 spaced apart to form a gap therebetween which is large enough to "clip" the NO-accumulation apparatus 300 over the rim of the bath unit, which rim is illustrated by a thick dashed line. The container 120 will therefore be arranged within the bath unit while the NO-supply 240 remains outside of the bath unit. The water circulation means 170, which can also assume the functions of the inlet 150 and the outlet 151 can thus generate water circulation from the container 120 into the bath unit and from the bath unit back into the container 120.

The NO-accumulation apparatus 300 as exemplarily illustrated in FIG. 4 may further include a heater (not shown) to heat the liquid 105 to a desired temperature.

The NO-accumulation apparatus 300 as exemplarily illustrated in FIG. 4 may further include a pressure sensor (not shown). In a particular aspect, the pressure sensor is positioned above the labelling 130.

Figure 5:
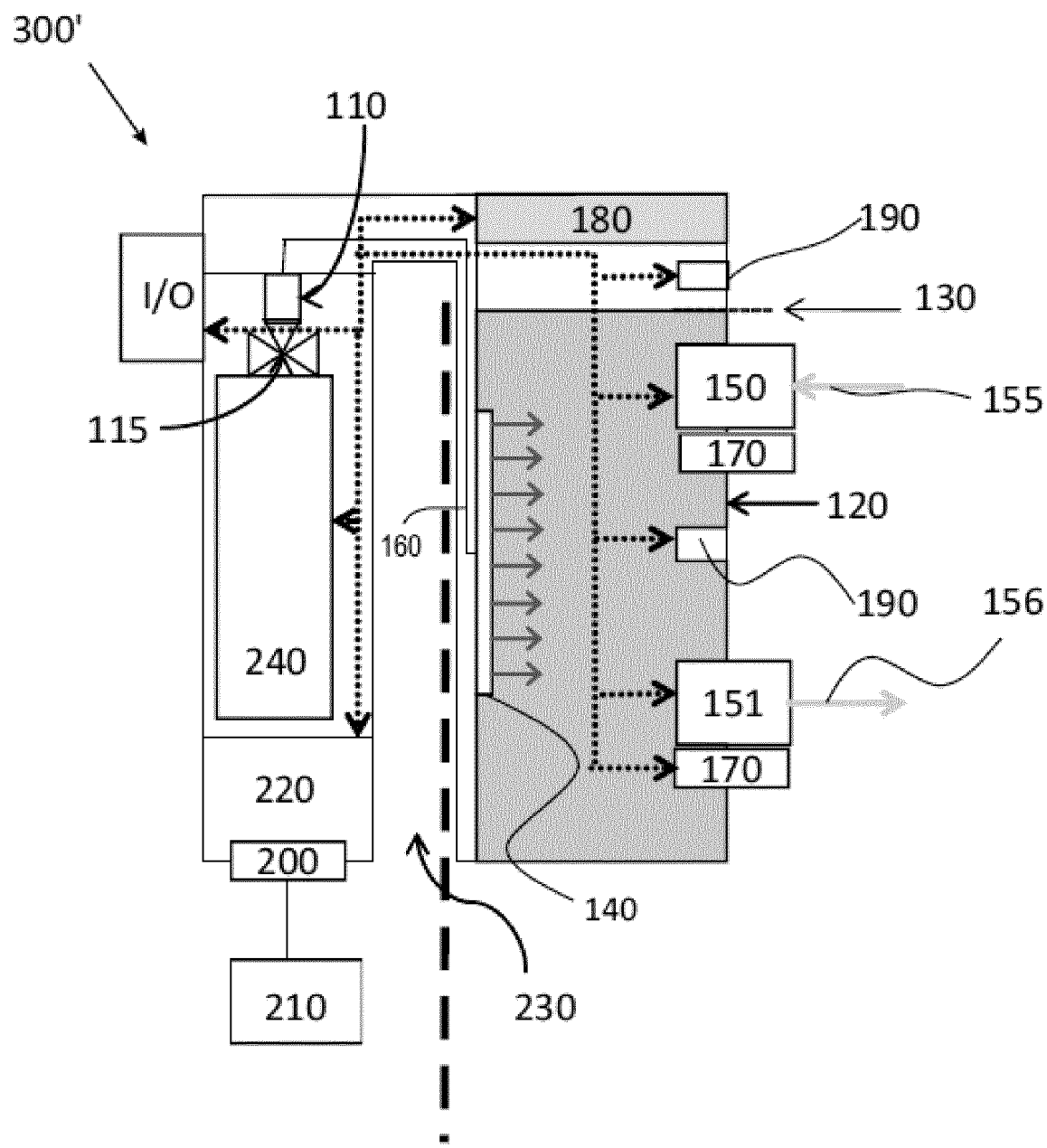
FIG. 5 illustrates a schematic perspective view of an NO-solution production apparatus according to an embodiment described herein.

With reference to FIG. 5, a further NO-solution production apparatus 300' is exemplarily shown. As illustrated, the NO-solution production apparatus 300' may include a NO-accumulation apparatus 100 as described herein and a gaseous NO-supply apparatus 240. Typically, the gaseous NO-supply apparatus 240 may include from 0.5 to 50 l gaseous NO, preferably from 1 to 30 l gaseous NO, more preferably from 3 to 20 l gaseous NO. The NO-solution production apparatus 300' may be controlled by a controller.

Figure 6:
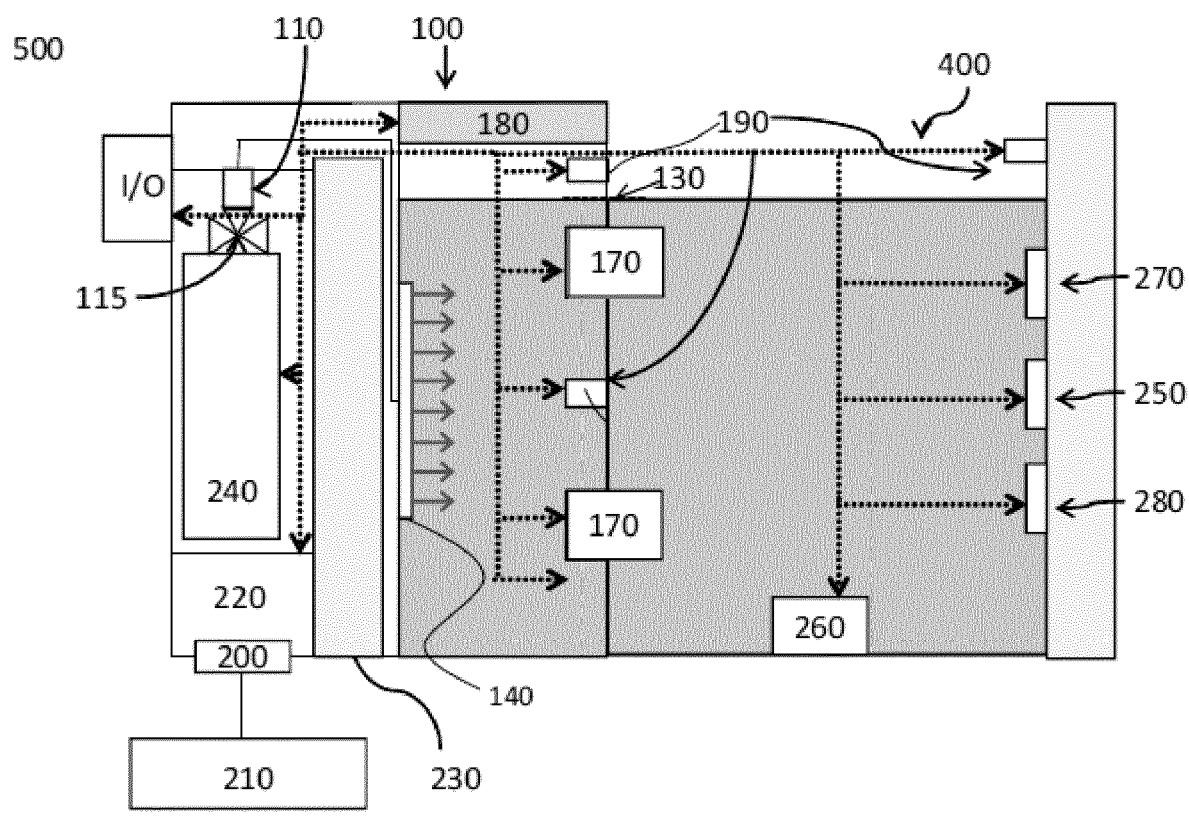
FIG. 6 illustrates a schematic perspective view of an NO-bath apparatus according to an embodiment described herein.

With reference to FIG. 6, a NO-bath apparatus is exemplarily shown. As illustrated, the NO-bath apparatus 500 may include an NO-solution production apparatus 300' as described herein and an immersion apparatus 400 such as a bath unit for immersing body parts of a mammal or articles. Typically, the NO-bath 500 may be controlled by a controller.

As illustrated in FIG. 6, the NO-accumulation apparatus 100 can be directly coupled with the bath unit 400 to form a single apparatus. More specifically, an outer wall portion of the NO-accumulation apparatus 100 can form a wall portion of the bath unit 400 so that the water circulation means 170 provides the direct fluidic communication between both compartments formed by the inner volume of the bath unit 400 and the container 120.

Figure 7:
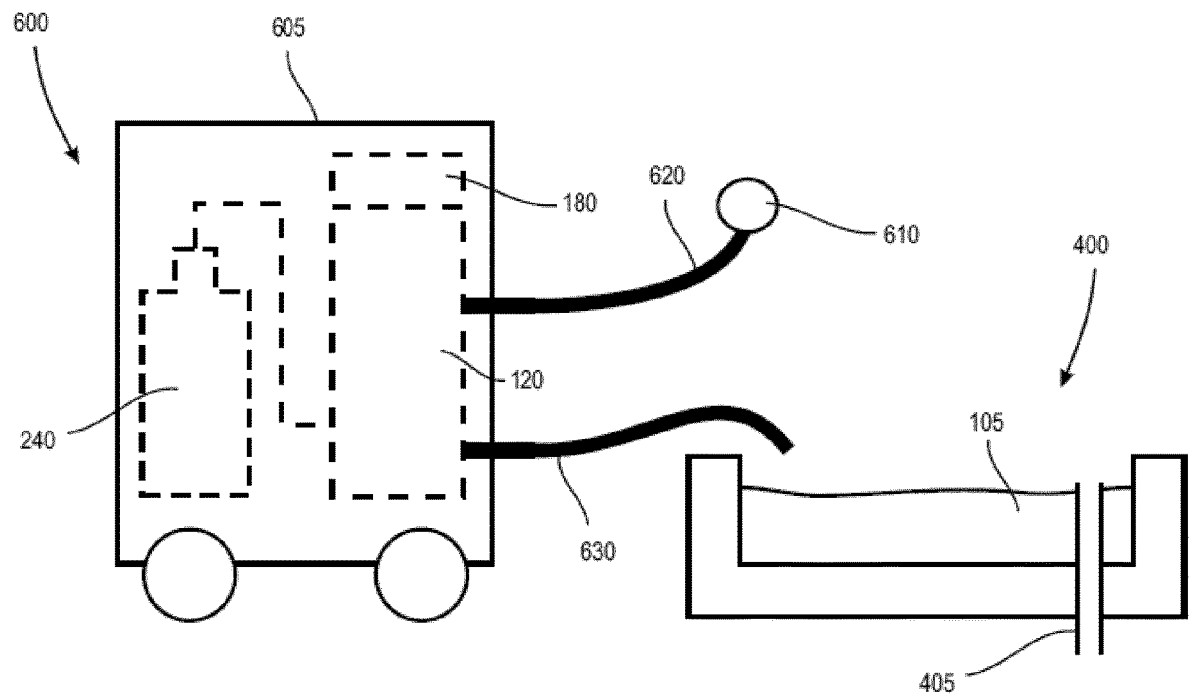
FIG. 7 illustrates a schematic perspective view of an NO-bath apparatus according to an embodiment described herein
Figure 8:
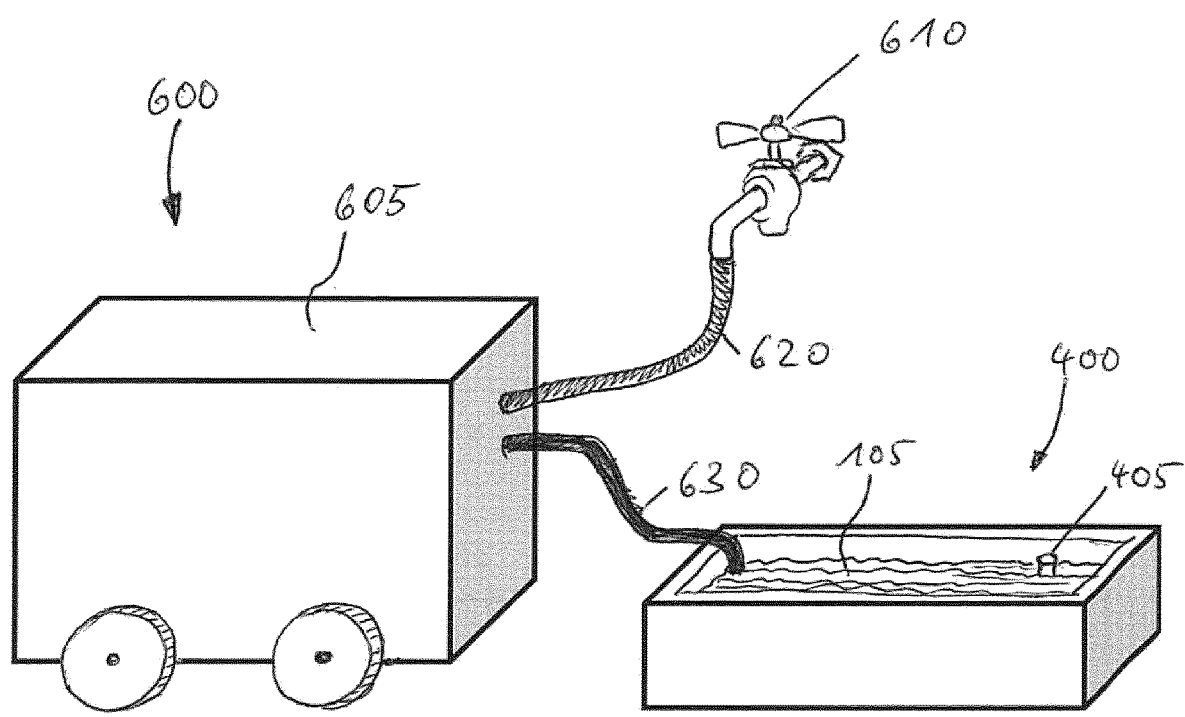
FIG. 8 illustrates a schematic perspective view of an NO-solution production apparatus according to an embodiment described herein used for delivery of NO-enriched water for treating medical conditions.
Figure 9:
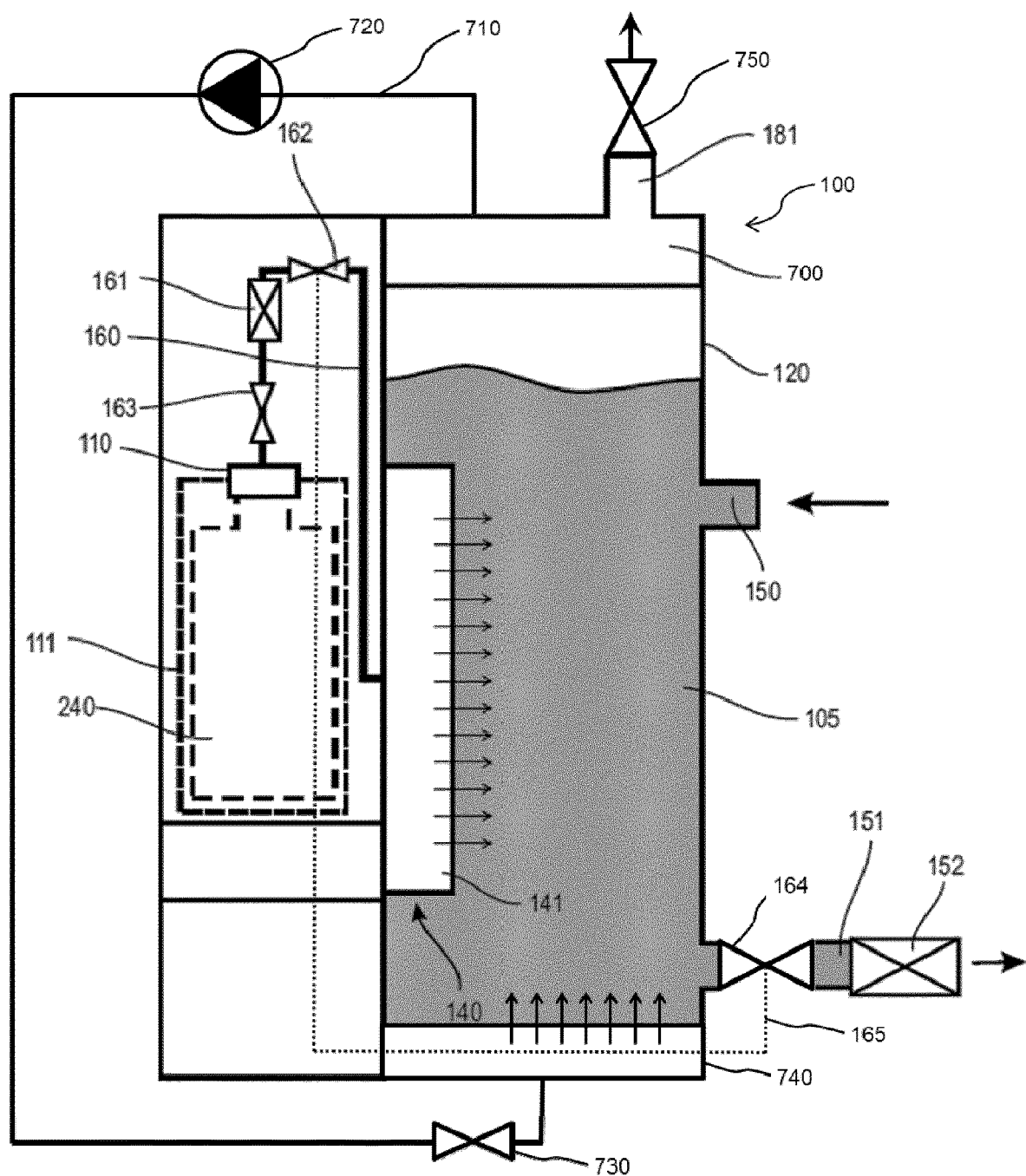
FIG. 9 illustrates a schematic perspective view of an NO-bath apparatus comprising means for uncoupling NO inflow from liquid removal and a NO-gas head 740 provided at the bottom of the container 105 according to an embodiment described herein.
Figure 10:
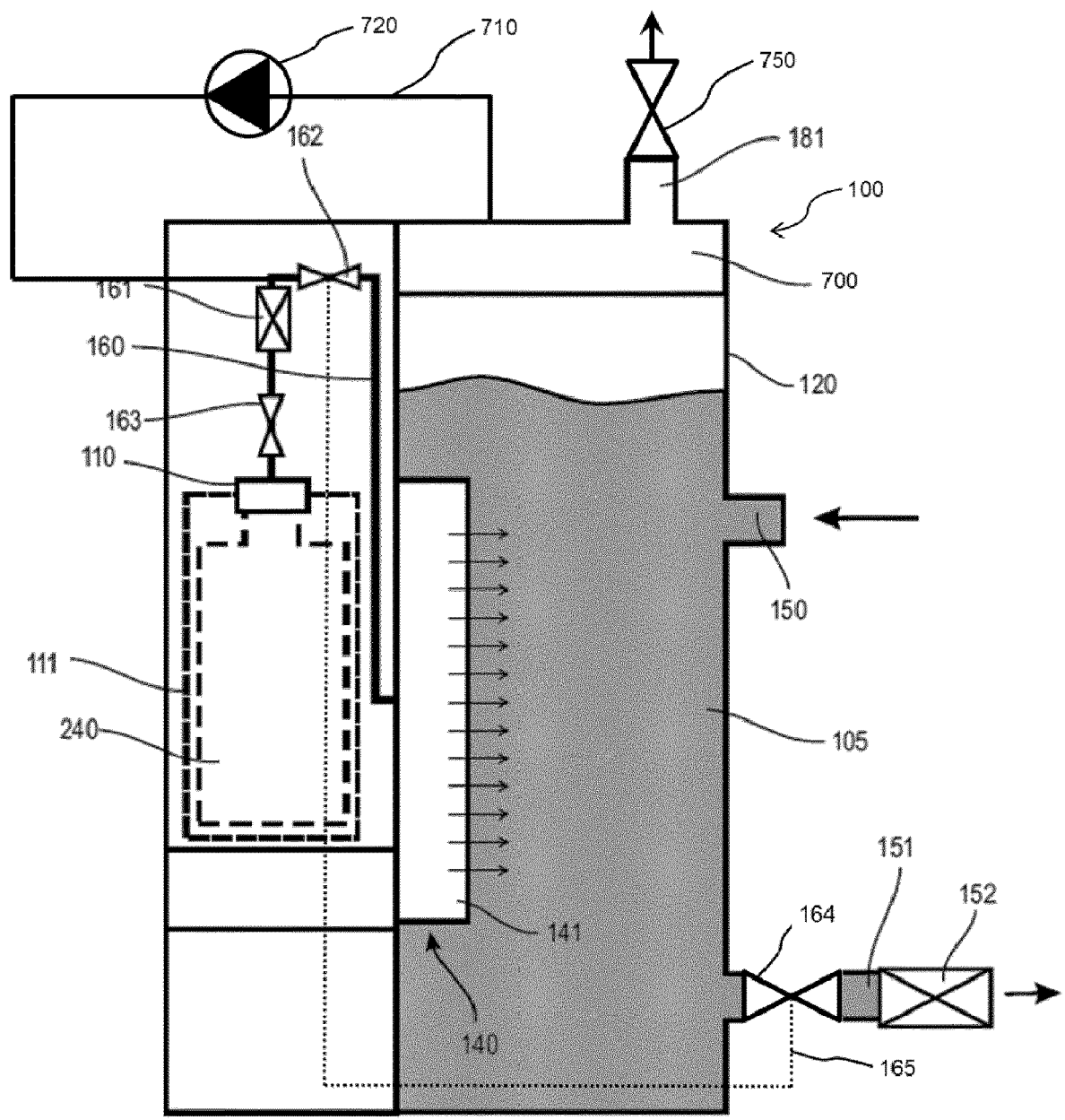
FIG. 10 illustrates a schematic perspective view of an NO-bath apparatus comprising means for uncoupling NO inflow from liquid removal and a NO-gas head 140 which is also used for the primary NO supply according to an embodiment described herein.
Figure 11:
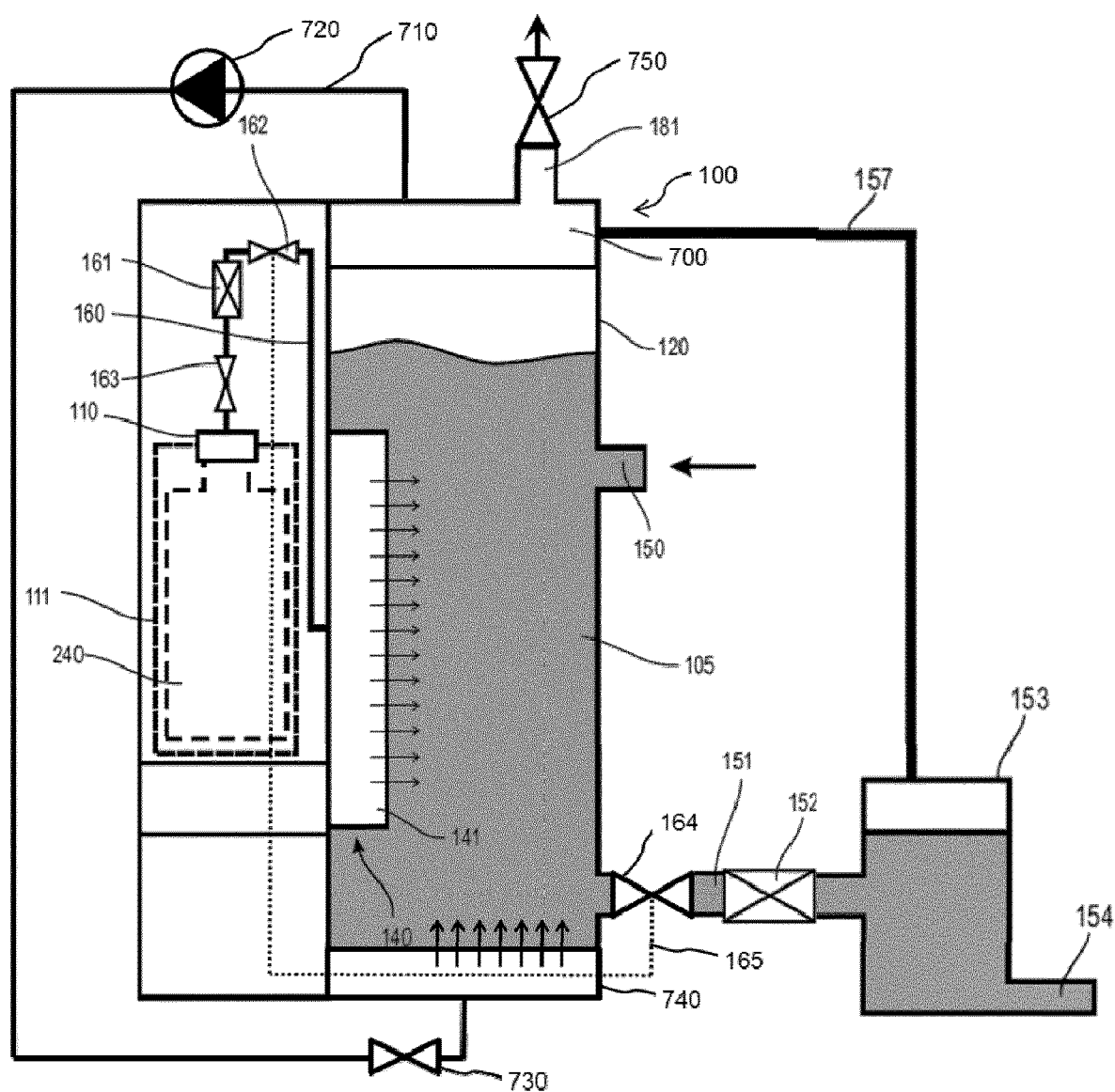
FIG. 11 illustrates a schematic perspective view of an NO-bath apparatus comprising means for uncoupling NO inflow from liquid removal having two NO-collecting units 153 and 700 which are fluidly coupled to the NO-gas head 740 according to an embodiment described herein.
Figure 12:
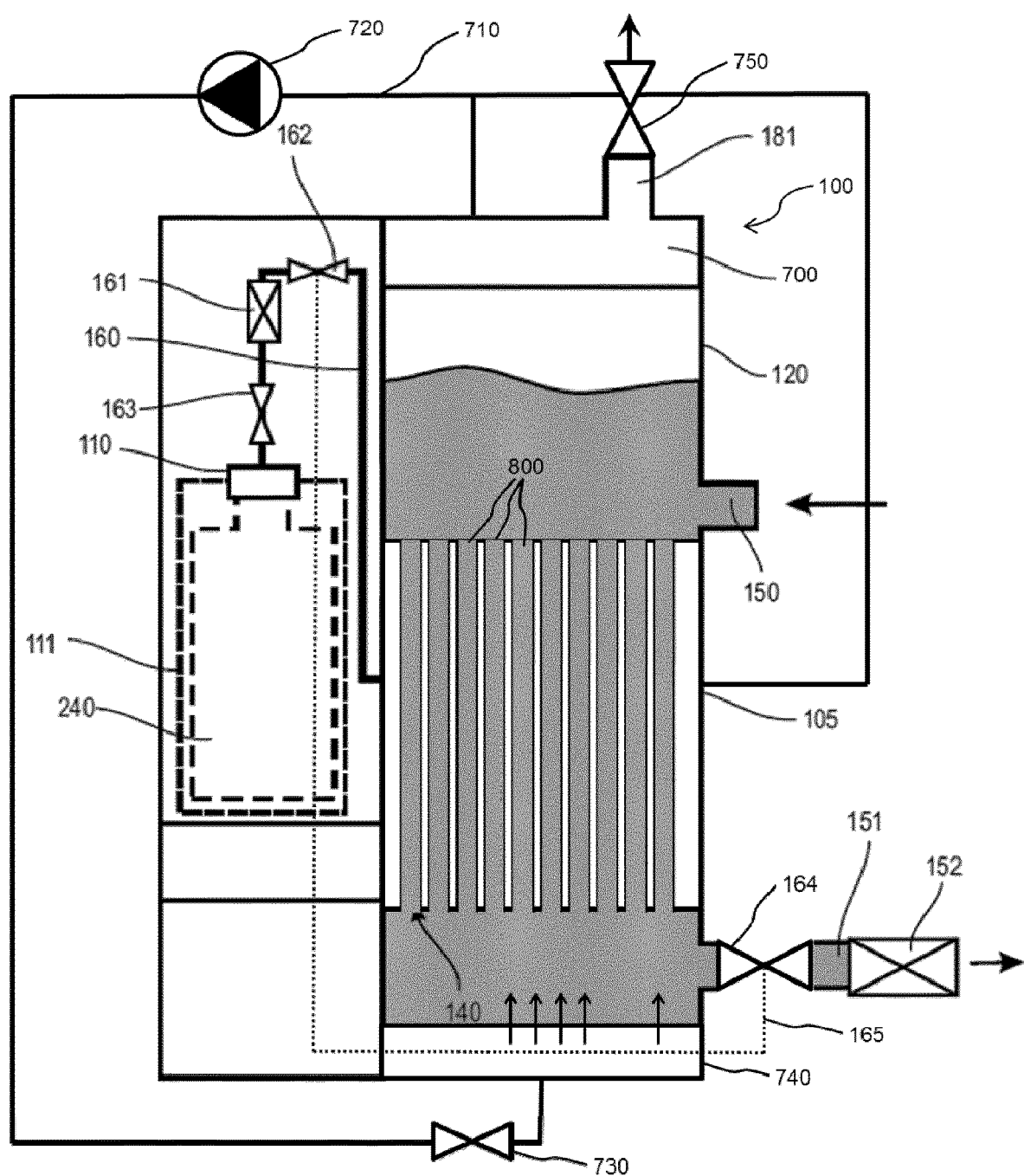
FIG. 12 illustrates a schematic perspective view of an NO-bath apparatus comprising a set of hollow fibers for supplying the NO gas to the liquid according to an embodiment described herein.
Figure 13:
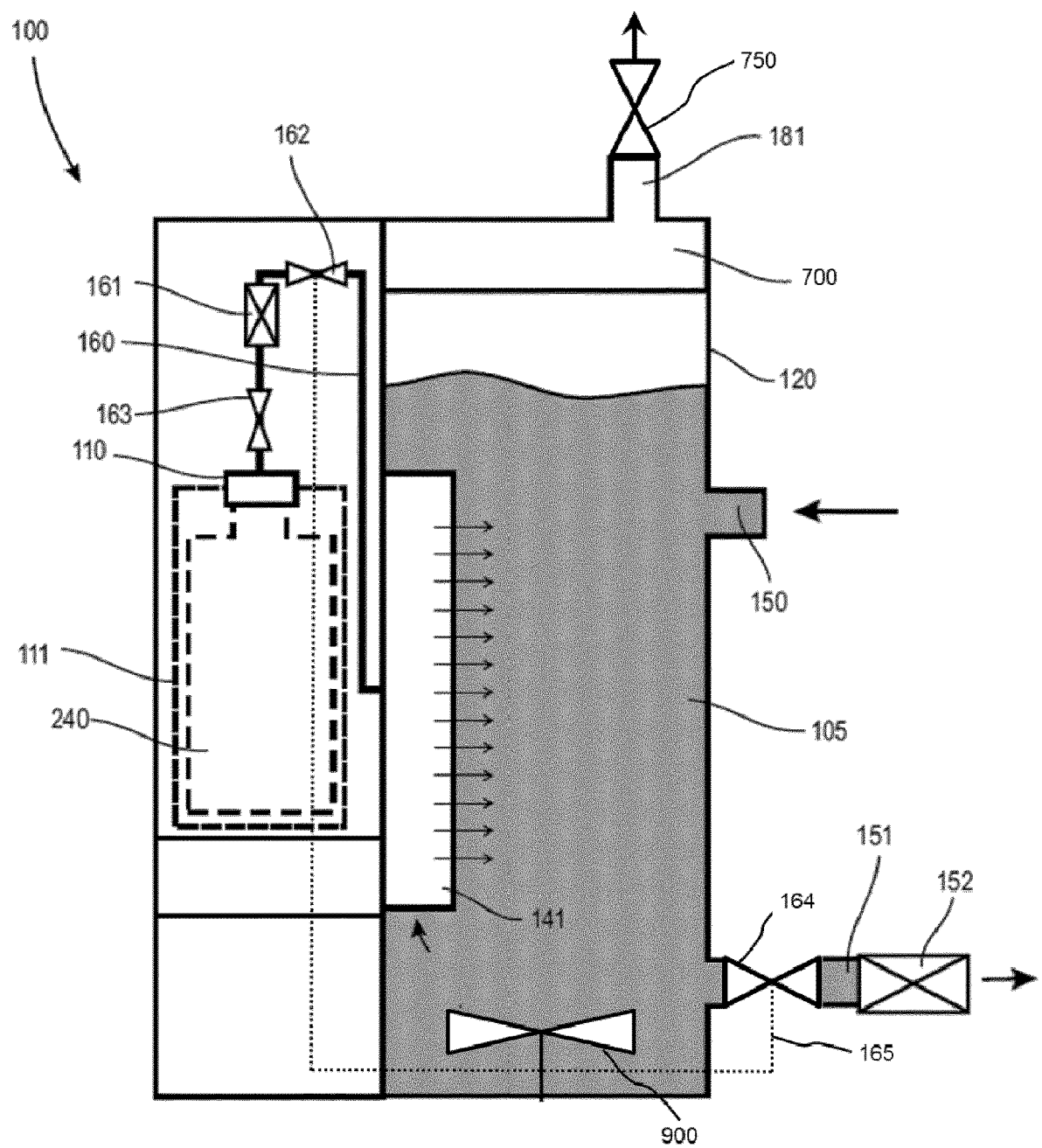
FIG. 13 illustrates a schematic perspective view of an NO-bath apparatus comprising a paddle mixer 900 as stirring device according to an embodiment described herein.
Figure 14:
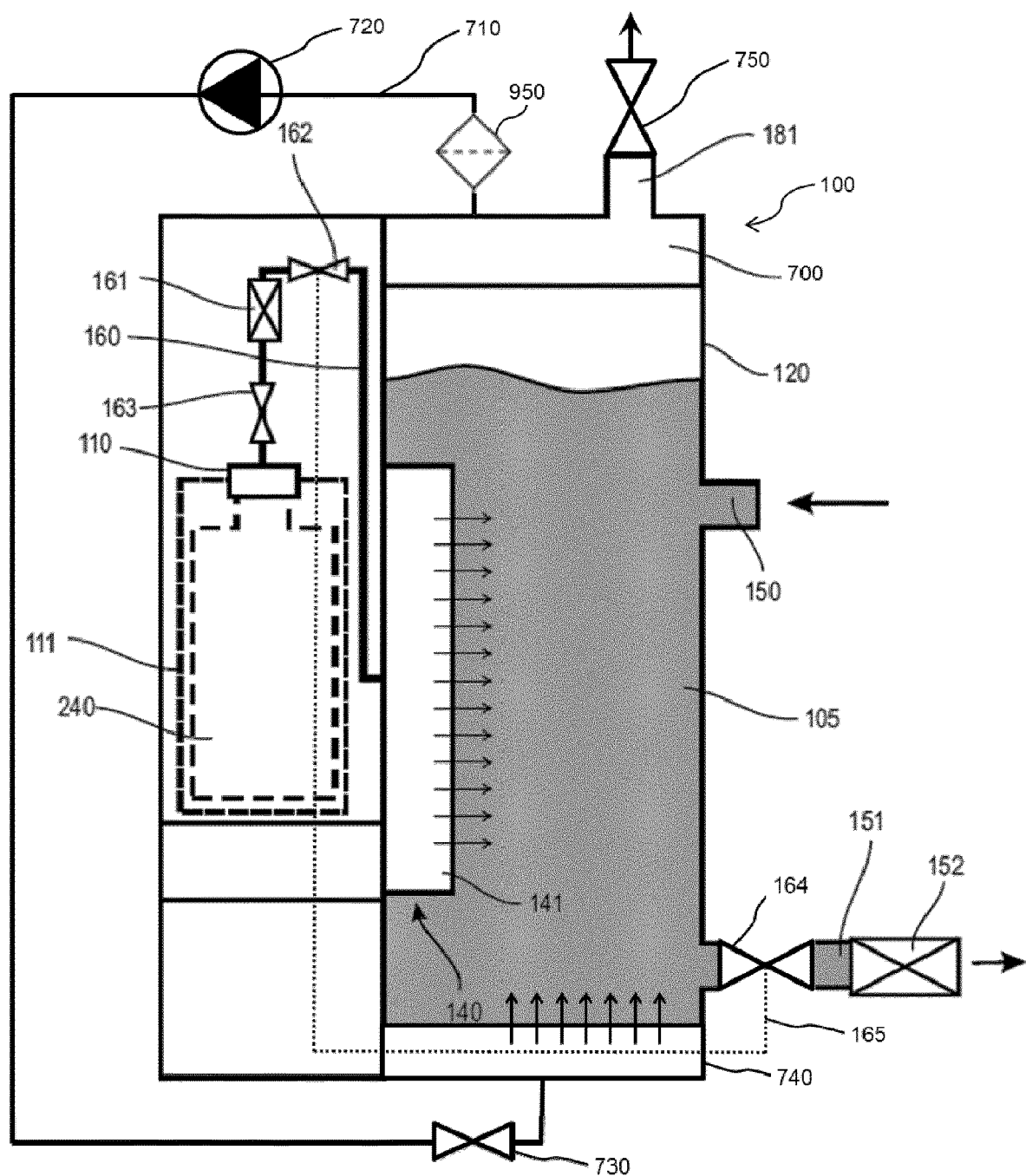
FIG. 14 illustrates a schematic perspective view of an NO-bath apparatus comprising a filter device 950 for filtering the NO gas removed from the NO gas collection unit according to an embodiment described herein.

FIG. 7 illustrates a mobile NO-solution production apparatus 600 which includes a housing 605 for accommodating the NO-gas supply 240, the container 120 and the NO-gas removal unit 180 to form a single apparatus that can be easily moved, for example on wheels.

The inlet of the container 120 is connected through a flexible hose with a water tap 610 to fed water into the container 120 and the outlet of the container 120 is connected with a flexible hose 630 that feeds the NO-containing water to an immobile bath unit 400, for example a ceramic or metallic foot bath which is installed in a care room of a hospital. The bath unit 400 includes a water overflow 405 that defines the filling height within the bath unit 400.

The NO-solution production apparatus 600 is a through-flow system as water is drawn from the tap 610, enriched with NO in the container 120 and then fed into the bath unit without a reflow into the container 120 from the bath unit 400. This is beneficial in terms of use and cleaning as no contaminated water 105 flows back into the container so that no filters are needed. The used water 105 can simply be disposed through the drains of the bath unit after the medical treatment and the bath unit 400 cleaned. Since freshly NO-enriched water 105 is continuously delivered to the bath unit, the NO-concentration in the water 105 can be maintained at constant level.

In a further embodiment of the invention the NO-accumulation apparatus comprises means for NO-recycling. Hereby, the NO that is outgassing from the NO containing liquid is collected and fed back to the liquid. This recycling mechanism has the advantage of reducing the NO consumption and also removing the necessity for providing an NO removing unit with e.g. a catalytic system for reducing NO, and/or NO-adsorber. Furthermore, this mechanism reduces the efforts for the design of the NO-gas dissolving unit. When using a NO-gas head with a plurality of nozzles or openings, the NO gas stream, especially when using larger nozzles or openings (e.g. with a diameter greater than 50 µm), tend to produce rather large NO bubbles that are not completely dissolved during their passage through the liquid. Hence, there could be a considerably amount of NO that will outgas from the liquid and can be refed into the liquid again. In sum, the recycling mechanism allow the use of nozzles/openings with larger diameter and/or the use of a slight overpressure and thereby reduces the engineering needs.

The NO-recycling means as outlined above comprises a NO-collection unit which is in fluid communication with a NO-gas dissolving unit comprising a NO-gas head.

The NO-collection unit is suitably identical with the NO-removing unit 180 and/or the gas-collection unit 153. Hereby, the means for fluid communication to the gas dissolving unit could be provided in addition to the disclosed gas outlets 154/181 or alternatively could replace these gas outlets 154 and 181. In another embodiment the NO-collection unit represents an additional component of the NO-accumulation apparatus.

In a preferred embodiment the NO-collection unit is located on the top of the container 120 or the intermediate container 158 since the outgassing NO will collect above the fluid surface.

The fluid communication between the NO-collection unit and the NO-gas dissolving unit is suitably provided by a gas line or a gas pipe. However, every gas-tight connection could be used therefore and can be implemented by the skilled person according to the requirements of the process.

As a preferred embodiment this fluid communication further comprises a pump device to provide a directed gas flow with the required pressure to the NO-gas dissolving unit. The fluid communication can further comprise on or more vessels to controlling the pressure of the NO gas and/or for preventing a back flow of the gas and/or preventing the generation of a negative pressure in the NO-gas collection unit which could lead to an undesired outgassing of NO.

In one embodiment of the invention the fluid communication further comprises a filter device to remove impurities from the NO gas. Since the most relevant impurity with regard to NO gas is $NO_2$ the filter is preferably suited to absorb $NO_2$ from the NO gas so that the NO gas is recycled in a purified form. The skilled person can rely on a broad spectrum of materials which at as nitrogen dioxide scavengers such as e.g. soda lime, polyphenylene sulfide polymers (such as "noXon" distributed by Hoechst AG, Frankfurt, Germany) and zeolite.

The NO gas is transported to an NO-gas dissolving unit. In one embodiment this unit is identical to the already established NO gas-dissolving unit 140. In another embodiment the collected NO is directed to a further NO gas-dissolving unit. This further NO gas dissolving unit can be designed as already described for the NO-gas dissolving unit 140. Hereby the two NO-gas dissolving units could use the same or different type of NO-gas heads. As an example the NO-gas-dissolving unit 140 could use a NO-permeable membrane and the NO gas dissolving unit of the recycling means a multitude of nozzles and opening.

In a preferred embodiment the NO-gas dissolving unit collection unit is located at the bottom of the container 120 so that the NO gas can transfer the complete liquid compartment and thereby increases the chance of achieving an optimized dissolution of the NO gas within said liquid.

In a further embodiment the NO-recycling mechanisms is uncoupled of the primary NO-gas dissolving mechanism. Hereby the NO-gas dissolving unit is used in a first step to use the NO gas provided by the NO-gas supply (so called "primary NO gas supply") in order to have a first accumulation of the NO gas within the liquid of the container. This initial delivery of NO gas might lead to an outgassing of NO. Hence, it might be beneficial to stop the influx of gas from the NO gas supply and to use the NO gas as collected in the NO-collection unit for further NO gas accumulation. This process could be performed iteratively so that a phase of primary NO gas supply is followed by a NO gas recycling which then is followed by a further primary NO gas supply.

In a further embodiment the pump device of the NO recycling unit can be used to generate a reduced pressure in the NO collection unit and therefore could induce the outgassing of gases which are present in the liquid before NO accumulation. This is of especially advantage when working with NO so that gases that react with NO such as oxygen can be reduced or even removed before starting to accumulate the NO within said liquid. Hereby, it is necessary to remove the collected gas (being primarily nitrogen and oxygen from the NO collection unit. Since these gases are not harmful they could be e.g. released into the surrounding. The initial outgassing has the further advantage that the solubility of NO is accordingly increased.

In a still further embodiment the NO recycling unit can be used by establishing a reduced pressure in order to remove NO from the liquid. This might be of advantage when the NO concentration should be reduced in the liquid to a desirable concentration or after the end of the application in order to "decontaminate" the NO containing liquid so that it could be safely retrieved and disposed. In this aspect the NO collection unit is coupled to or comprises means for NO removal.

In another embodiment the pump of the NO recycling unit is regulated by the NO gas pressure of the NO collection unit. As a result, only superfluous NO gas is removed from the NO collection unit while not further inducing the outgassing of NO from the aqueous liquid within the container 120. This can be accomplished, if the pump removes the NO gas of the NO collection unit as soon as a certain NO gas pressure value is reached and the pump activity is then stopped when the NO gas pressure as result of the pumping activity falls below a certain NO gas pressure value.

In a further aspect, the invention provides a method for accumulating NO in a liquid using the NO-accumulation apparatus of the invention and comprising the following steps:
  a. Degassing of the liquid by use of the NO recycling means
  b. Primary NO influx as taken from NO gas supply
  c. NO influx as taken from NO collection unit
  d. Optionally repeating steps b and c
  e. Degassing of NO from the liquid Instead of delivering the NO-enriched water 105 to a bath unit, it is also possible to fed the NO-enriched water to a water shower or a spray unit, for example to ultimately distribute the NO-containing water on the skin of a patient.

Moreover, the NO-enriched water 105 can be temporarily stored in a tank which can be removably connected with the NO-gas accumulation apparatus. The NO-enriched water 105 stored in the tank can then be fed into the bath unit or to the above mentioned shower or spray unit. It is furthermore possible that the tank, when filled with the NO-enriched water, is moved to a treatment site such as a fixedly installed (built-in) bath.

As used herein, the term "mammal" may refer to primates, bovines, ovines, caprines, ungulates, porcines, equines, felines, canines, lagomorphs, pinnipeds, rodents. Typically, the mammal is a human. Human subjects include both males and females and subjects of all ages including fetal, neonatal, infant, juvenile, adolescent, adult, and geriatric humans.

As used herein, the term "article" may refer to instruments which may be implements employed in patient contact (human or veterinary) during the practice of surgery, medicine, dentistry, podiatry, pathology, for therapeutic, diagnostic and/or research purposes. Exemplary articles include surgical instruments, such as scalpels, probes, clamps, endoscopes, operating room or dental hand pieces, ventilation tubes. Other exemplary articles include medical devices such as contact lenses, implantable medical devices, dental implants and appliances, and dentures.

Typically, the immersion apparatus 500 or NO-bath apparatus further includes at least one of a heater 250, a sinkhole 260, a NO-sensor 190, a pH sensor 270 and a temperature sensor 280.

According to a further embodiment of the present disclosure, a method is provided for accumulating NO in a liquid. The method includes the steps of feeding gaseous NO from a gaseous NO-supply into a NO-accumulation apparatus with the help of the gas dissolving unit, and accumulating gaseous NO in the liquid. Additionally or alternatively, gaseous NO may also be accumulated in a gas such as air in the NO-accumulation apparatus.

According to a further embodiment of the present disclosure, the NO-accumulation apparatus as described herein can be used in the treatment of diseases/disorders. Typical diseases/disorders which can be treated with the NO-accumulation apparatus as described herein may be dermatological conditions.

Exemplary dermatological conditions include wounds, burns, atopic dermatitis, contact dermatitis, chicken pox, psoriasis, impetigo, secondary skin infections, bed sores, diabetic foot ulcers, venous leg ulcers, surgical incisions, acne vulgaris, truncal acne and/or cystic nodular acne, onychomycosis, tinea pedis, tinea cruris, tinea capitis, molluscum contagiosum, common and genital warts, and any combination thereof. The NO-accumulation apparatus as described herein may be used to treat other skin ailments, either via anti-microbial action, anti-inflammatory action, or by any other mechanism.

According to a particular embodiment of the present disclosure, the NO-accumulation apparatus as described herein can be used for stimulating the metabolism of tissues by topical application in humans and animals, for treating diabetic foot wounds; for treating surgical or accidental wounds, for treating chronic, non-healing and/or poorly healing wounds; for treating bacterial and/or fungal wound infections; for treating dermatological diseases selected from inflammatory, immunologically controlled and auto-immune diseases; for treating diabetic feet and wounds; for treating neuropathic pain in diabetes; for treating varicose veins; for treating local, superficial and deep-seated ischemia and thrombopathic diseases of tissues; for treating acute and chronic inflammation of the skin; for treating allergies of the skin; for treating parasitic infections of the skin; for treating atopic dermatitis eczema, in particular dermatomyositis, pemphigus vulgaris and/or other local and systemic infections and/or both acute and chronic inflammatory situations; for treating wound defects, such as chronic diabetic neuropathic ulcer, ulcus cruris, decubitus ulcers; for treating larger areas of the body for the therapy of systemic diseases such as increased blood pressure (hypertension) and related hemodynamic disorders; for treating secondary healing infected wounds, primary healing wounds, especially ablative cracks or abrasions, for treating patients with (skin) grafts; for treating diabetic pain of the lower extremities (feet or leg); and for treating poorly perfused flaps.

Other therapeutic agents, such as those that have anti-inflammatory, pain-relieving, immunosuppressant, vasodilating; wound healing and/or anti-biofilm forming properties may be used in combination with the NO-accumulation apparatus as described herein.

According to a further embodiment of the present disclosure, the NO-accumulation apparatus as described herein can be used to disinfect articles, such as those described above.

In view of the forgoing description, the following embodiments are disclosed, inter alia, herein which can be combined with any other embodiments described herein.

Embodiment 1

An NO-accumulation apparatus configured to accumulate gaseous NO in a liquid, wherein the NO-accumulation apparatus includes a gas port configured to couple with a gaseous NO-supply apparatus. The NO-accumulation apparatus can further include the container as described above, and/or the NO-gas removal unit. Furthermore, the NO-accumulation apparatus can optionally include an NO-sensor for measuring NO in water. Furthermore, the NO-accumulation apparatus can optionally include a pressure sensor for measuring the pressure within the container so that, when the pressure exceeds a given value, the NO-gas supply can be reduced.

Embodiment 2

An NO-accumulation apparatus configured to accumulate gaseous NO in a liquid, wherein the NO-accumulation apparatus includes a container which includes a gas dissolving unit configured to feed gaseous NO from a gaseous NO-supply apparatus into the container. The NO-accumulation apparatus can optionally include an NO-sensor for measuring NO in water. Furthermore, the NO-accumulation apparatus can optionally include a pressure sensor for measuring the pressure within the container.

Embodiment 3

An NO-accumulation apparatus configured to accumulate gaseous NO in a liquid, wherein the NO-accumulation apparatus includes at least one catalytic system for the reduction of NO. The catalytic system can form the NO-gas removal unit as described above. The NO-accumulation apparatus can optionally include an NO-sensor for measuring NO in water. Furthermore, the NO-accumulation apparatus can optionally include a pressure sensor for measuring the pressure within the container.

Embodiment 4

An NO-accumulation apparatus configured to accumulate gaseous NO in a liquid wherein the NO-accumulation apparatus includes at least one NO-sensor configured to determine the NO-concentration. The NO-accumulation apparatus can include a container as described above in which the NO-sensor is arranged.

Embodiment 5

An NO-accumulation apparatus configured to accumulate gaseous NO in a liquid for use in the treatment of diseases or medical conditions such as any of the above described medical conditions.

Embodiment 6

An NO-accumulation apparatus configured to accumulate gaseous NO in a liquid wherein the NO-accumulation apparatus includes a container having at least one inlet and at least one outlet, wherein the at least one inlet is configured to add liquid into the container, wherein the at least one outlet is configured to remove liquid from the container into an immersion apparatus for immersing body parts of a mammal or articles.

Embodiment 7

An NO-solution production apparatus having an NO-accumulation apparatus configured to accumulate gaseous NO in a liquid to form a NO-solution, a gaseous NO-supply apparatus configured to supply gaseous NO, and a gas dissolving unit configured to feed the gaseous NO from the gaseous NO-supply apparatus into the NO-accumulation apparatus.

Embodiment 8

An NO-bath having an NO-solution production apparatus as defined in any of the preceding embodiments, and an immersion apparatus for immersing body parts of a mammal or articles.

Embodiment 9

A method for accumulating NO in a liquid, including feeding gaseous NO from a gaseous NO-supply into a NO-accumulation apparatus with the help of gas dissolving unit; and accumulating gaseous NO in the liquid.

Embodiment 10

An NO-accumulation apparatus according to any of the above embodiments, further including a container.

Embodiment 11

An NO-accumulation apparatus according to any of the above embodiments, wherein the container includes gas dissolving unit.

Embodiment 12

An NO-accumulation apparatus according to any of the above embodiments, wherein the gas dissolving unit are nozzles.

Embodiment 13

An NO-accumulation apparatus according to any of the above embodiments, wherein the nozzles are arranged in a predetermined pattern.

Embodiment 14

An NO-accumulation apparatus according to any of the above embodiments, wherein the gas dissolving unit is a porous material.

Embodiment 15

An NO-accumulation apparatus according to any of the above embodiments, wherein the container further includes water circulation means.

Embodiment 16

NO-accumulation apparatus according to any of the above embodiments, wherein the water circulation means are water circulation turbines.

Embodiment 17

An NO-accumulation apparatus according to any of the above embodiments, wherein the container includes at least one inlet configured to add liquid into the container and at least one outlet configured to remove liquid from the container.

Embodiment 18

An NO-accumulation apparatus according to any of the above embodiments, wherein the container extends along an axial direction and consists of one or more portions which are a non-detachably connected with each other.

Embodiment 19

An NO-accumulation apparatus according to any of the above embodiments, wherein the container includes at least one cap detachably connected to the container, wherein the at least one cap is configured to provide a sealed container.

Embodiment 20

An NO-accumulation apparatus according to any of the above embodiments, wherein the liquid is an aqueous liquid.

Embodiment 21

An NO-accumulation apparatus according to any of the above embodiments, wherein the aqueous liquid is water.

Embodiment 22

An NO-accumulation apparatus according to any of the above embodiments, further including a catalytic system for the reduction of NO. The catalytic system for the reduction of NO is an example of the above described NO-gas removal unit.

Embodiment 23

An NO-accumulation apparatus according to any of the above embodiments, wherein the catalytic system is a selective catalytic reduction system (SCR).

Embodiment 24

An NO-accumulation apparatus according to any of the above embodiments, wherein the catalytic system catalyzes the reduction of NO to $N_2$, $H_2O$ and $CO_2$.

Embodiment 25

An NO-accumulation apparatus according to any of the above embodiments, further including a NO-absorber configured to absorb gaseous NO. The NO-absorber is an example of the above described NO-gas removal unit.

Embodiment 26

An NO-accumulation apparatus according to any of the above embodiments, further including at least one NO-sensor configured to determine the NO-concentration in the liquid and/or in the NO-gas removal unit.

Embodiment 27

An NO-accumulation apparatus according to any of the above embodiments, wherein the at least one NO-sensor is configured to determine the NO-concentration in air, for example outside of the bath unit to inform the personnel or the patient when the NO-concentration in the ambient exceeds a given allowable value.

Embodiment 28

An NO-accumulation apparatus according to any of the above embodiments, wherein the at least one NO-sensor is configured to determine the NO-concentration in a liquid.

Embodiment 29

An NO-accumulation apparatus according to any of the above embodiments, further including a gas port for coupling with a power supply.

Embodiment 30

An NO-accumulation apparatus according to any of the above embodiments, wherein the NO-accumulation apparatus is controlled by a controller.

Embodiment 31

An NO-accumulation apparatus according to any of the above embodiments, further including a gas port for coupling with an immersion apparatus.

Embodiment 32

An NO-accumulation apparatus according to any of the above embodiments configured to accumulate gaseous NO in a liquid and gaseous NO in a gas.

Embodiment 33

An NO-accumulation apparatus according to any of the above embodiments, wherein the NO-accumulation apparatus includes a gas port configured to couple with an immersion apparatus, wherein the gas port has a U shape.

Embodiment 34

An NO-accumulation apparatus according to any of the above embodiments, wherein the NO-accumulation apparatus includes a heater.

Embodiment 35

An NO-accumulation apparatus according to any of the above embodiments, wherein the NO-accumulation apparatus includes a pressure sensor.

Embodiment 36

An NO-accumulation apparatus according to any of the above embodiments, wherein the gas port includes a thread to which the gaseous NO-supply apparatus can be mounted.

Embodiment 37

An NO-solution production apparatus according to any of the above embodiments, wherein the gaseous NO-supply apparatus includes 0.5 to 50 l gaseous NO.

Embodiment 38

An NO-bath according to any of the above embodiments, wherein the immersion apparatus includes at least one of a heater, a sinkhole, a NO-sensor, a pH sensor and a temperature sensor.

Embodiment 39

An NO-accumulation apparatus or NO-solution production apparatus according to any of the above embodiments, further including a tank which is removably connected with the NO-gas accumulation apparatus.

Embodiment 40

Use of the NO-accumulation apparatus according to any of the above embodiments for disinfecting articles.

While the foregoing is directed to embodiments of the invention, other and further embodiments of the invention may be devised without departing from the basic scope thereof, and the scope thereof is determined by the claims that follow.

REFERENCE LIST 100, 300, 600 NO-accumulation apparatus
105 liquid/water
110 gas port
111 carrier unit
115 thread
120 container
130 labeling
140 NO-gas dissolving unit
141 NO-gas head
142 chamber of NO-gas head
143 wall of NO-gas head
144 nozzle/pore/opening
145 inlet port of NO-gas head
146 porous body
146a inner porous layer
146b outer porous layer
147 external support
148 opening
149 internal support
150 inlet
151 outlet
152 pressure reducer
153 gas-collecting unit
154 outlet port
155 inflow
156 outflow
157 NO-gas return feeding
160 NO-gas feeding
161 pressure reducer
162 control valve
163 high pressure valve
164 outlet valve
165 mechanical, electrical or electronical coupling between the two valves 162 and 164
170 water circulation means
180 NO-gas removal unit/catalytic system/NO-absorber
181 gas outlet
190 NO-gas sensor
200 connector
210 power supply
220 controller/controller unit
230 coupling member
240 NO-gas supply
250 heater
270 pH-sensor
280 temperature sensor
400 bath unit
405 water overflow
500 NO-bath apparatus
300', 600 NO-solution production apparatus
605 housing
610 tap
620 inlet hose
630 outlet hose
700 NO-collection unit
710 NO gas line
720 pump
730 valve
740 NO gas head of recycling unit
750 outlet valve
800 hollow fibers
900 stirring device
950 filter device

The invention claimed is:

1. An NO-accumulation apparatus for accumulating NO in a liquid, comprising:
a container defining a cavity for accommodating the liquid, an inlet for feeding the liquid into the container and an outlet for delivering the liquid from the container to a bath unit;
an NO-gas dissolving unit for dissolving gaseous NO in the liquid to produce an NO-containing liquid, wherein the NO-gas dissolving unit is arranged in the container and/or forms a part of the container; and
an NO-gas port in fluid communication with the NO-gas dissolving unit, said NO-gas port being adapted to couple with an NO-gas supply; and first decoupling means for decoupling an inflow of NO-gas to the liquid within the container and second decoupling means for decoupling removal of the NO-containing liquid from the container;

wherein the first and second decoupling means are mechanically, electrically or electronically coupled such that the inflow of the NO-gas to the liquid within the container is inhibited when the NO-containing liquid is being removed from the container and such that removal of the NO-containing liquid from the container is inhibited when NO-gas is flowing into the liquid in the container.

2. The NO-accumulation apparatus according to claim 1, wherein the first and second decoupling means are shut-off devices.

3. The NO-accumulation apparatus according to claim 2, wherein the shut-off devices are selected from the group consisting of valves, shutter valves, shutoff dampers and stopcocks.

4. The NO-accumulation apparatus according to claim 1, wherein the NO-gas dissolving unit comprises an NO-gas head with a plurality of openings through which NO-gas can flow or diffuse into the liquid.

5. The NO-accumulation apparatus according to claim 4, wherein the NO-gas head comprises a chamber having a wall for separating the NO-gas from the liquid, wherein the wall includes a plurality of nozzles which forms the plurality of openings.

6. The NO-accumulation apparatus according to claim 4, wherein the NO-gas head comprises a porous portion with an open cell porosity, wherein the pores of the porous portion form the plurality of openings.

7. The NO-accumulation apparatus according to claim 6, wherein the porous portion is comprised of at least of one of
an open-porous inorganic material, and
an open-porous organic material.

8. The NO-accumulation apparatus according to claim 1, wherein the NO-gas dissolving unit comprises a plurality of hollow fiber membranes.

9. The NO accumulation apparatus according to claim 1, further comprising means for NO recycling such that NO which is outgassing from the NO-containing liquid is collected and fed back to the liquid within the container.

10. The NO accumulation apparatus according to claim 9, wherein the means for NO recycling comprises an NO-collection unit which is in fluid communication with an NO-gas dissolving unit.

11. The NO-accumulation apparatus according to claim 9, wherein the means for NO recycling further comprises at least one of or both of a valve and a pump.

12. The NO-accumulation apparatus according to claim 1, wherein the NO-accumulation apparatus is adapted to maintain a pressure above ambient pressure in the container and to dissolve the NO-gas in the liquid under pressure, and wherein the outlet is connected to, or comprises, a pressure reducer for reducing the pressure of the liquid to ambient pressure.

13. The NO-accumulation apparatus according to claim 1, further comprising at least one NO-gas pressure reducer forming part of the fluid communication between the NO-gas port and the NO-gas dissolving unit.

14. The NO-accumulation apparatus according to claim 1, further comprising an NO-removal unit for removing excess NO that is not dissolved in the liquid, wherein the NO-removal unit is at least one of
a catalytic system for reducing NO, and
an NO-adsorber.

15. The NO-accumulation apparatus according to claim 1, further comprising at least one of
an NO-sensor adapted to detect the concentration of NO dissolved in the liquid,
a pressure sensor adapted to detect the pressure within the container,
a pH sensor adapted to detect the pH-value in the liquid,
a temperature sensor adapted to detect the temperature of the liquid,
a heater for heating the liquid,
a liquid circulation unit for circulating the liquid within the container,
a liquid circulation unit for circulating the liquid between the container and a bath unit when the bath unit is in fluid communication with the inlet and the outlet of the container, and
a pumping unit for pumping liquid from the container.

16. The NO-accumulation apparatus according to claim 1, further comprising a control unit adapted to control the flow of NO from the NO-gas port to the NO-gas dissolving unit.

17. An NO-solution production apparatus, comprising:
an NO-accumulation apparatus according to claim 1; and
a pressurized NO-gas supply coupled to the NO-gas port of the NO-accumulation apparatus.

18. The NO-solution production apparatus according to claim 17, wherein the pressurized NO-gas supply is a compressed NO-gas cylinder having a volume for accommodating compressed NO-gas of less than 2 liters.

19. An NO-bath apparatus, comprising:
an NO-accumulation apparatus according to claim 1; and
a bath unit for accommodating an NO-containing liquid and for immersing one or more body parts of a mammal or a human, or articles into the NO-containing liquid.

20. A method for treating a medical condition in a patient comprising contacting skin of the patient with an NO-containing liquid obtained from an apparatus according to claim 1, wherein the medical condition is selected from the group consisting of:
stimulating metabolism of tissues by topical application in humans and animals;
treating diabetic foot wounds;
treating surgical or accidental wounds;
treating chronic, non-healing and/or poorly healing wounds;
treating bacterial and/or fungal wound infections;
treating dermatological diseases selected from inflammatory, immunologically controlled and autoimmune diseases;
treating diabetic feet and wounds;
treating neuropathic pain in diabetes;
treating varicose veins;
treating local superficial and deep-seated ischemia and thrombopathic diseases of tissues;
treating acute and chronic inflammation of the skin;
treating allergies of the skin;
treating parasitic infections of the skin;
treating atopic dermatitis eczema, dermatomyositis, pemphigus vulgaris and/or other local and systemic infections and/or both acute and chronic inflammatory situations;
treating wound defects, chronic diabetic neuropathic ulcer, leg ulcers, ulcus cruris, decubitus ulcers;
treating large body areas for therapy of systemic diseases, blood pressure and related hemodynamic disorders;
treating secondary healing infected wounds, primary healing wounds, ablative cracks or abrasions;

treating patients with skin grafts;
treating diabetic pain of lower extremities; and
treating poorly perfused flaps.

21. A method for accumulating gaseous NO in a liquid, comprising:
providing a container;
feeding a liquid into the container;
feeding pressurized NO-gas into the liquid contained in the container to accumulate NO in the liquid, wherein a pressure within the container is optionally maintained at a pressure above ambient pressure; and whereby a first decoupling means prevents removal of the liquid from the container as long as pressurized NO gas is fed into the container; and
feeding the NO-accumulated liquid to a bath unit, whereby a second decoupling means, that is mechanically, electrically or electronically coupled to the first decoupling means, prevents the inflow of NO gas into the container as long as the NO-accumulated liquid is fed into a bath unit.

22. An NO-bath apparatus, comprising:
an NO-solution production apparatus according to claim 17; and
a bath unit for accommodating an NO-containing liquid and for immersing one or more body parts of a mammal or a human, or articles into the NO-containing liquid.

* * * * *